(12) United States Patent
Stacchino et al.

(10) Patent No.: US 9,867,695 B2
(45) Date of Patent: Jan. 16, 2018

(54) MINIMALLY-INVASIVE CARDIAC-VALVE PROSTHESIS

(71) Applicant: Sorin Group Italia S.r.l., Milan (IT)

(72) Inventors: Carla Stacchino, Turin (IT); Giovanni Bergamasco, Turin (IT); Gaetano Burriesci, London (GB)

(73) Assignee: Sorin Group Italia S.r.l., Milan (IT)

( * ) Notice: Subject to any disclaimer, the term of this patent is extended or adjusted under 35 U.S.C. 154(b) by 622 days.

(21) Appl. No.: 13/963,191

(22) Filed: Aug. 9, 2013

(65) Prior Publication Data

US 2013/0325112 A1    Dec. 5, 2013

Related U.S. Application Data

(63) Continuation of application No. 12/139,683, filed on Jun. 16, 2008, now Pat. No. 8,535,373, which is a (Continued)

(30) Foreign Application Priority Data

Mar. 3, 2004    (IT) .............................. TO2004A0135

(51) Int. Cl.
*A61F 2/24*    (2006.01)
(52) U.S. Cl.
CPC .......... *A61F 2/2412* (2013.01); *A61F 2/2418* (2013.01); *A61F 2/2427* (2013.01)
(58) Field of Classification Search
CPC ........ A61F 2/24; A61F 2/2409; A61F 2/2418; A61F 2/2427; A61F 2/243; A61F 2/2433; A61F 2/2436; A61F 2/2412
See application file for complete search history.

(56) References Cited

U.S. PATENT DOCUMENTS 3,143,742 A   8/1964   Cromie
3,334,629 A   8/1967   Cohn
(Continued)

FOREIGN PATENT DOCUMENTS

CN    101011298 A    8/2007
DE    3640745 A1    6/1987
(Continued)

OTHER PUBLICATIONS

Grube, Eberhard et al., Case Report entitled "First Report on a Human Percutaneous Transluminal Implantation of a Self-Expanding Valve Prosthesis for Interventional Treatment of Aortic Valve Stenosis", Valvular Heart Disease, Catheterization and Cardiovascular Interventions, 2005, 66:465-469.
(Continued)

*Primary Examiner* — Christopher D Prone
(74) *Attorney, Agent, or Firm* — Faegre Baker Daniels LLP

(57) ABSTRACT

A cardiac-valve prosthesis is adapted for percutaneous implantation. The prosthesis includes an armature adapted for deployment in a radially expanded implantation position, the armature including a support portion and an anchor portion, which are substantially axially coextensive with respect to one another. A set of leaflets is coupled to the support portion. The leaflets can be deployed with the armature in the implantation position. The leaflets define, in the implantation position, a flow duct that is selectably obstructable. The anchor portion can be deployed to enable anchorage of the cardiac-valve prosthesis at an implantation site.

20 Claims, 3 Drawing Sheets

Related U.S. Application Data continuation of application No. 11/066,346, filed on Feb. 25, 2005, now Pat. No. 8,109,996.

(56) References Cited

U.S. PATENT DOCUMENTS

| | | | |
|---|---|---|---|
| 3,363,442 A | 1/1968 | Kennedy et al. |
| 3,409,013 A | 11/1968 | Berry |
| 3,540,431 A | 11/1970 | Mobin-Uddin |
| 3,546,710 A | 12/1970 | Shumakov et al. |
| 3,574,865 A | 4/1971 | Hamaker |
| 3,587,115 A | 6/1971 | Shiley |
| 3,608,097 A | 9/1971 | Bellhouse et al. |
| 3,628,535 A | 12/1971 | Ostrowsky et al. |
| 3,642,004 A | 2/1972 | Osthagen et al. |
| 3,657,744 A | 4/1972 | Ersek |
| 3,671,979 A | 6/1972 | Moulopoulos |
| 3,744,060 A | 7/1973 | Bellhouse et al. |
| 3,755,823 A | 9/1973 | Hancock |
| 3,795,246 A | 3/1974 | Sturgeon |
| 3,839,741 A | 10/1974 | Haller |
| 3,868,956 A | 3/1975 | Alfidi et al. |
| 3,874,388 A | 4/1975 | King et al. |
| 3,997,923 A | 12/1976 | Possis |
| 4,035,849 A | 7/1977 | Angell et al. |
| 4,056,854 A | 11/1977 | Boretos et al. |
| 4,086,665 A | 5/1978 | Poirier |
| 4,106,129 A | 8/1978 | Carpentier et al. |
| 4,222,126 A | 9/1980 | Boretos et al. |
| 4,233,690 A | 11/1980 | Akins |
| 4,265,694 A | 5/1981 | Boretos et al. |
| 4,291,420 A | 9/1981 | Reul |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,425,908 A | 1/1984 | Simon |
| 4,451,936 A | 6/1984 | Carpentier et al. |
| 4,470,157 A | 9/1984 | Love |
| 4,477,930 A | 10/1984 | Totten et al. |
| 4,501,030 A | 2/1985 | Lane |
| 4,506,394 A | 3/1985 | Bedard |
| 4,574,803 A | 3/1986 | Storz |
| 4,580,568 A | 4/1986 | Gianturco |
| 4,592,340 A | 6/1986 | Boyles |
| 4,610,688 A | 9/1986 | Silvestrini et al. |
| 4,612,011 A | 9/1986 | Kautzky |
| 4,624,822 A | 11/1986 | Arru et al. |
| 4,647,283 A | 3/1987 | Carpentier et al. |
| 4,648,881 A | 3/1987 | Carpentier et al. |
| 4,655,218 A | 4/1987 | Kulik et al. |
| 4,662,885 A | 5/1987 | DiPisa, Jr. |
| 4,665,906 A | 5/1987 | Jervis |
| 4,681,908 A | 7/1987 | Broderick et al. |
| 4,692,164 A | 9/1987 | Dzemeshkevich et al. |
| 4,710,192 A | 12/1987 | Liotta et al. |
| 4,758,151 A | 7/1988 | Arru et al. |
| 4,777,951 A | 10/1988 | Cribier et al. |
| 4,787,899 A | 11/1988 | Lazarus |
| 4,796,629 A | 1/1989 | Grayzel |
| 4,797,901 A | 1/1989 | Goerne et al. |
| 4,819,751 A | 4/1989 | Shimada et al. |
| 4,834,755 A | 5/1989 | Silvestrini et al. |
| 4,856,516 A | 8/1989 | Hillstead |
| 4,872,874 A | 10/1989 | Taheri |
| 4,878,495 A | 11/1989 | Grayzel |
| 4,878,906 A | 11/1989 | Lindemann et al. |
| 4,883,458 A | 11/1989 | Shiber |
| 4,909,252 A | 3/1990 | Goldberger |
| 4,917,102 A | 4/1990 | Miller et al. |
| 4,922,905 A | 5/1990 | Strecker |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,002,559 A | 3/1991 | Tower |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,042,161 A | 8/1991 | Hodge |
| 5,047,041 A | 9/1991 | Samuels |
| 5,059,177 A | 10/1991 | Towne et al. |
| 5,061,273 A | 10/1991 | Yock |
| 5,084,151 A | 1/1992 | Vallana et al. |
| 5,085,635 A | 2/1992 | Cragg |
| 5,089,015 A | 2/1992 | Ross |
| 5,123,919 A | 6/1992 | Sauter et al. |
| 5,133,845 A | 7/1992 | Vallana et al. |
| 5,139,515 A | 8/1992 | Robicsek |
| 5,152,771 A | 10/1992 | Sabbaghian et al. |
| 5,161,547 A | 11/1992 | Tower |
| 5,163,953 A | 11/1992 | Vince |
| 5,163,954 A | 11/1992 | Curcio et al. |
| 5,167,628 A | 12/1992 | Boyles |
| 5,217,483 A | 6/1993 | Tower |
| 5,232,445 A | 8/1993 | Bonzel |
| 5,272,909 A | 12/1993 | Nguyen et al. |
| 4,733,665 B1 | 1/1994 | Palmaz |
| 5,295,958 A | 3/1994 | Shturman |
| 5,300,086 A | 4/1994 | Gory et al. |
| 5,314,468 A | 5/1994 | Ramos Martinez |
| 5,327,774 A | 7/1994 | Nguyen et al. |
| 5,332,402 A | 7/1994 | Teitelbaum |
| 5,350,398 A | 9/1994 | Pavcnik et al. |
| 5,360,014 A | 11/1994 | Sauter et al. |
| 5,370,684 A | 12/1994 | Vallana et al. |
| 5,370,685 A | 12/1994 | Stevens |
| 5,387,247 A | 2/1995 | Vallana et al. |
| 5,389,106 A | 2/1995 | Tower |
| 5,397,351 A | 3/1995 | Pavcnik et al. |
| 5,411,552 A | 5/1995 | Andersen et al. |
| 5,415,633 A | 5/1995 | Lazarus et al. |
| 5,423,886 A | 6/1995 | Arru et al. |
| 5,431,676 A | 7/1995 | Dubrul et al. |
| 5,443,446 A | 8/1995 | Shturman |
| 5,449,384 A | 9/1995 | Johnson |
| 5,480,424 A | 1/1996 | Cox |
| 5,489,294 A | 2/1996 | McVenes et al. |
| 5,489,296 A | 2/1996 | Love et al. |
| 5,489,297 A | 2/1996 | Duran |
| 5,496,346 A | 3/1996 | Horzewski et al. |
| 5,505,689 A | 4/1996 | Kramer et al. |
| 5,507,767 A | 4/1996 | Maeda et al. |
| 4,954,126 B1 | 5/1996 | Wallsten |
| 5,522,884 A | 6/1996 | Wright |
| 5,545,209 A | 8/1996 | Roberts et al. |
| 5,545,211 A | 8/1996 | An et al. |
| 5,545,214 A | 8/1996 | Stevens |
| 5,545,215 A | 8/1996 | Duran |
| 4,655,771 B1 | 9/1996 | Wallsten |
| 5,554,185 A | 9/1996 | Block et al. |
| 5,560,487 A | 10/1996 | Starr |
| 5,575,818 A | 11/1996 | Pinchuk |
| 5,580,922 A | 12/1996 | Park et al. |
| 5,591,195 A | 1/1997 | Taheri et al. |
| 5,609,626 A | 3/1997 | Quijano et al. |
| 5,645,559 A | 7/1997 | Hachtman et al. |
| 5,665,115 A | 9/1997 | Cragg |
| 5,667,523 A | 9/1997 | Bynon et al. |
| 5,669,919 A | 9/1997 | Sanders et al. |
| 5,672,169 A | 9/1997 | Verbeek |
| 5,674,277 A | 10/1997 | Freitag |
| 5,693,066 A | 12/1997 | Rupp et al. |
| 5,695,498 A | 12/1997 | Tower |
| 5,698,307 A | 12/1997 | Levy |
| 5,702,368 A | 12/1997 | Stevens et al. |
| 5,712,953 A | 1/1998 | Langs |
| 5,713,953 A | 2/1998 | Vallana et al. |
| 5,716,417 A | 2/1998 | Girard et al. |
| 5,746,709 A | 5/1998 | Rom et al. |
| 5,749,890 A | 5/1998 | Shaknovich |
| 5,766,151 A | 6/1998 | Valley et al. |
| 5,776,187 A | 7/1998 | Krueger et al. |
| 5,782,809 A | 7/1998 | Umeno et al. |

(56) References Cited

U.S. PATENT DOCUMENTS

| | | |
|---|---|---|
| 5,800,456 A | 9/1998 | Maeda et al. |
| 5,800,508 A | 9/1998 | Goicoechea et al. |
| 5,800,531 A | 9/1998 | Cosgrove et al. |
| 5,807,405 A | 9/1998 | Vanney et al. |
| 5,810,873 A | 9/1998 | Morales |
| 5,814,096 A | 9/1998 | Lam et al. |
| 5,817,126 A | 10/1998 | Imran |
| 5,824,037 A | 10/1998 | Fogarty et al. |
| 5,824,041 A | 10/1998 | Lenker et al. |
| 5,824,043 A | 10/1998 | Cottone, Jr. |
| 5,824,053 A | 10/1998 | Khosravi et al. |
| 5,824,055 A | 10/1998 | Spiridigliozzi et al. |
| 5,824,056 A | 10/1998 | Rosenberg |
| 5,824,061 A | 10/1998 | Quijano et al. |
| 5,824,064 A | 10/1998 | Taheri |
| 5,840,081 A | 11/1998 | Andersen et al. |
| 5,843,158 A | 12/1998 | Lenker et al. |
| 5,843,244 A | 12/1998 | Pelton et al. |
| 5,851,232 A | 12/1998 | Lois |
| 5,855,597 A | 1/1999 | Jayaraman |
| 5,855,601 A | 1/1999 | Bessler et al. |
| 5,860,996 A | 1/1999 | Urban et al. |
| 5,861,028 A | 1/1999 | Angell |
| 5,868,783 A | 2/1999 | Tower |
| 5,876,436 A | 3/1999 | Vanney et al. |
| 5,876,448 A | 3/1999 | Thompson et al. |
| 5,885,228 A | 3/1999 | Rosenman et al. |
| 5,888,201 A | 3/1999 | Stinson et al. |
| 5,891,191 A | 4/1999 | Stinson |
| 5,891,195 A | 4/1999 | Klostermeyer et al. |
| 5,906,619 A | 5/1999 | Olson et al. |
| 5,907,893 A | 6/1999 | Zadno Azizi et al. |
| 5,913,842 A | 6/1999 | Boyd et al. |
| 5,925,063 A | 7/1999 | Khosravi |
| 5,944,738 A | 8/1999 | Amplatz et al. |
| 5,947,993 A | 9/1999 | Morales |
| 5,951,540 A | 9/1999 | Verbeek |
| 5,954,766 A | 9/1999 | Zadno Azizi et al. |
| 5,957,949 A | 9/1999 | Leonhardt et al. |
| 5,968,068 A | 10/1999 | Dehdashtian et al. |
| 5,972,016 A | 10/1999 | Morales |
| 5,980,570 A | 11/1999 | Simpson |
| 5,984,957 A | 11/1999 | Laptewicz, Jr. et al. |
| 5,997,573 A | 12/1999 | Quijano et al. |
| 6,010,531 A | 1/2000 | Donlon et al. |
| 6,019,739 A | 2/2000 | Rhee et al. |
| 6,019,790 A | 2/2000 | Holmberg et al. |
| 6,022,370 A | 2/2000 | Tower |
| 6,024,737 A | 2/2000 | Morales |
| 6,027,525 A | 2/2000 | Suh et al. |
| 6,029,671 A | 2/2000 | Stevens et al. |
| 6,042,589 A | 3/2000 | Marianne |
| 6,042,598 A | 3/2000 | Tsugita et al. |
| 6,042,607 A | 3/2000 | Williamson, IV et al. |
| 6,051,002 A | 4/2000 | Morales |
| 6,051,104 A | 4/2000 | Oriaran et al. |
| 6,059,809 A | 5/2000 | Amor et al. |
| 6,059,827 A | 5/2000 | Fenton, Jr. |
| 6,063,102 A | 5/2000 | Morales |
| 6,110,200 A | 8/2000 | Hinnenkamp |
| 6,110,201 A | 8/2000 | Quijano et al. |
| 6,146,366 A | 11/2000 | Schachar |
| 6,159,239 A | 12/2000 | Greenhalgh |
| 6,162,208 A | 12/2000 | Hipps |
| 6,162,245 A | 12/2000 | Jayaraman |
| 6,168,614 B1 | 1/2001 | Andersen et al. |
| 6,171,335 B1 | 1/2001 | Wheatley et al. |
| 6,187,016 B1 | 2/2001 | Hedges et al. |
| 6,197,143 B1 | 3/2001 | Bodnar |
| 6,200,336 B1 | 3/2001 | Pavcnik et al. |
| 6,202,272 B1 | 3/2001 | Jackson |
| 6,203,550 B1 | 3/2001 | Olson |
| 6,210,408 B1 | 4/2001 | Chandrasekaran et al. |
| 6,218,662 B1 | 4/2001 | Tchakarov et al. |
| 6,221,006 B1 | 4/2001 | Dubrul et al. |
| 6,221,091 B1 | 4/2001 | Khosravi |
| 6,241,757 B1 | 6/2001 | An et al. |
| 6,245,102 B1 | 6/2001 | Jayaraman |
| 6,248,116 B1 | 6/2001 | Chevillon et al. |
| 6,258,114 B1 | 7/2001 | Konya et al. |
| 6,258,115 B1 | 7/2001 | Dubrul |
| 6,258,120 B1 | 7/2001 | McKenzie et al. |
| 6,270,526 B1 | 8/2001 | Cox |
| 6,277,110 B1 | 8/2001 | Morales |
| 6,277,555 B1 | 8/2001 | Duran et al. |
| 6,287,339 B1 | 9/2001 | Vazquez et al. |
| 6,299,637 B1 | 10/2001 | Shaolian et al. |
| 6,299,638 B1 | 10/2001 | Sauter |
| 6,302,906 B1 | 10/2001 | Goicoechea et al. |
| 6,309,382 B1 | 10/2001 | Garrison et al. |
| 6,309,383 B1 | 10/2001 | Campbell et al. |
| 6,309,417 B1 | 10/2001 | Spence et al. |
| 6,312,462 B1 | 11/2001 | McDermott et al. |
| 6,338,735 B1 | 1/2002 | Stevens |
| 6,348,063 B1 | 2/2002 | Yassour et al. |
| 6,350,277 B1 | 2/2002 | Kocur |
| 6,350,281 B1 | 2/2002 | Rhee |
| 6,352,547 B1 | 3/2002 | Brown et al. |
| 6,352,554 B2 | 3/2002 | De Paulis |
| 6,352,708 B1 | 3/2002 | Duran et al. |
| 6,371,970 B1 | 4/2002 | Khosravi et al. |
| 6,371,983 B1 | 4/2002 | Lane |
| 6,379,383 B1 | 4/2002 | Palmaz et al. |
| 6,380,457 B1 | 4/2002 | Yurek et al. |
| 6,387,117 B1 | 5/2002 | Arnold, Jr. et al. |
| 6,398,807 B1 | 6/2002 | Chouinard et al. |
| 6,402,780 B2 | 6/2002 | Williamson, IV et al. |
| 6,409,750 B1 | 6/2002 | Hyodoh et al. |
| 6,424,885 B1 | 7/2002 | Niemeyer et al. |
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,303 B1 | 10/2002 | Amplatz et al. |
| 6,475,239 B1 | 11/2002 | Campbell et al. |
| 6,481,262 B2 | 11/2002 | Ching et al. |
| 6,482,228 B1 | 11/2002 | Norred |
| 6,488,704 B1 | 12/2002 | Connelly et al. |
| 6,493,608 B1 | 12/2002 | Niemeyer |
| 6,494,909 B2 | 12/2002 | Greenhalgh |
| 6,503,272 B2 | 1/2003 | Duerig et al. |
| 6,506,201 B2 | 1/2003 | Di Caprio et al. |
| 6,508,833 B2 | 1/2003 | Pavcnik et al. |
| 6,510,722 B1 | 1/2003 | Ching et al. |
| 6,527,800 B1 | 3/2003 | McGuckin, Jr. et al. |
| 6,530,949 B2 | 3/2003 | Konya et al. |
| 6,544,285 B1 | 4/2003 | Thubrikar et al. |
| 6,562,031 B2 | 5/2003 | Chandrasekaran et al. |
| 6,562,058 B2 | 5/2003 | Seguin et al. |
| 6,569,196 B1 | 5/2003 | Vesely |
| 6,582,462 B1 | 6/2003 | Andersen et al. |
| 6,585,758 B1 | 7/2003 | Chouinard et al. |
| 6,592,546 B1 | 7/2003 | Barbut et al. |
| 6,598,307 B2 | 7/2003 | Love et al. |
| 6,605,112 B1 | 8/2003 | Moll et al. |
| 6,613,077 B2 | 9/2003 | Gilligan et al. |
| 6,622,604 B1 | 9/2003 | Chouinard et al. |
| 6,629,350 B2 | 10/2003 | Motsenbocker |
| 6,635,068 B1 | 10/2003 | Dubrul et al. |
| 6,652,571 B1 | 11/2003 | White et al. |
| 6,652,578 B2 | 11/2003 | Bailey et al. |
| 6,656,213 B2 | 12/2003 | Solem |
| 6,656,219 B1 | 12/2003 | Wiktor |
| 6,663,663 B2 | 12/2003 | Kim et al. |
| 6,669,724 B2 | 12/2003 | Park et al. |
| 6,673,089 B1 | 1/2004 | Yassour et al. |
| 6,673,109 B2 | 1/2004 | Cox |
| 6,676,684 B1 | 1/2004 | Morley et al. |
| 6,676,692 B2 | 1/2004 | Rabkin et al. |
| 6,676,698 B2 | 1/2004 | McGuckin, Jr. et al. |
| 6,678,962 B1 | 1/2004 | Love et al. |
| 6,679,893 B1 | 1/2004 | Tran |
| 6,682,558 B2 | 1/2004 | Tu et al. |

(56) References Cited

U.S. PATENT DOCUMENTS

| | | |
|---|---|---|
| 6,685,739 B2 | 2/2004 | DiMatteo et al. |
| 6,689,144 B2 | 2/2004 | Gerberding |
| 6,689,164 B1 | 2/2004 | Seguin |
| 6,692,512 B2 | 2/2004 | Jang |
| 6,692,513 B2 | 2/2004 | Streeter et al. |
| 6,695,878 B2 | 2/2004 | McGuckin, Jr. et al. |
| 6,702,851 B1 | 3/2004 | Chinn et al. |
| 6,716,241 B2 | 4/2004 | Wilder et al. |
| 6,719,789 B2 | 4/2004 | Cox |
| 6,726,713 B2 | 4/2004 | Schaldach, Jr. et al. |
| 6,730,118 B2 | 5/2004 | Spenser et al. |
| 6,730,377 B2 | 5/2004 | Wang |
| 6,733,525 B2 | 5/2004 | Yang et al. |
| 6,736,846 B2 | 5/2004 | Cox |
| 6,752,828 B2 | 6/2004 | Thornton |
| 6,758,855 B2 | 7/2004 | Fulton, III et al. |
| 6,769,161 B2 | 8/2004 | Brown et al. |
| 6,769,434 B2 | 8/2004 | Liddicoat et al. |
| 6,786,925 B1 | 9/2004 | Buchanan et al. |
| 6,790,229 B1 | 9/2004 | Berreklouw |
| 6,790,230 B2 | 9/2004 | Beyersdorf et al. |
| 6,792,979 B2 | 9/2004 | Konya et al. |
| 6,797,002 B2 | 9/2004 | Spence et al. |
| 6,805,711 B2 | 10/2004 | Quijano et al. |
| 6,821,297 B2 | 11/2004 | Snyders |
| 6,830,575 B2 | 12/2004 | Stenzel et al. |
| 6,830,584 B1 | 12/2004 | Seguin |
| 6,830,585 B1 | 12/2004 | Artof et al. |
| 6,846,324 B2 | 1/2005 | Stobie |
| 6,846,325 B2 | 1/2005 | Liddicoat |
| 6,866,650 B2 | 3/2005 | Stevens et al. |
| 6,872,223 B2 | 3/2005 | Roberts et al. |
| 6,875,231 B2 | 4/2005 | Anduiza et al. |
| 6,883,522 B2 | 4/2005 | Spence et al. |
| 6,887,266 B2 | 5/2005 | Williams et al. |
| 6,890,330 B2 | 5/2005 | Streeter et al. |
| 6,893,460 B2 | 5/2005 | Spenser et al. |
| 6,896,690 B1 | 5/2005 | Lambrecht et al. |
| 6,908,481 B2 | 6/2005 | Cribier |
| 6,913,600 B2 | 7/2005 | Valley et al. |
| 6,915,560 B2 | 7/2005 | Austin |
| 6,929,653 B2 | 8/2005 | Strecter |
| 6,936,066 B2 | 8/2005 | Palmaz et al. |
| 6,939,365 B1 | 9/2005 | Fogarty et al. |
| 6,951,571 B1 | 10/2005 | Srivastava |
| 6,966,924 B2 | 11/2005 | Holmberg |
| 6,968,607 B2 | 11/2005 | Motsenbocker |
| 6,974,474 B2 | 12/2005 | Pavcnik et al. |
| 6,974,476 B2 | 12/2005 | McGuckin, Jr. et al. |
| 6,981,982 B2 | 1/2006 | Armstrong et al. |
| 6,986,742 B2 | 1/2006 | Hart et al. |
| 6,988,881 B2 | 1/2006 | Motsenbocker et al. |
| 6,989,027 B2 | 1/2006 | Allen et al. |
| 6,989,028 B2 | 1/2006 | Lashinski et al. |
| 6,991,649 B2 | 1/2006 | Sievers |
| 7,007,396 B2 | 3/2006 | Rudko et al. |
| 7,018,401 B1 | 3/2006 | Hyodoh et al. |
| 7,018,404 B2 | 3/2006 | Holmberg et al. |
| 7,018,406 B2 | 3/2006 | Seguin et al. |
| 7,021,114 B2 | 4/2006 | Perreault |
| 7,041,128 B2 | 5/2006 | McGuckin, Jr. et al. |
| 7,044,966 B2 | 5/2006 | Svanidze et al. |
| 7,048,014 B2 | 5/2006 | Hyodoh et al. |
| 7,069,794 B2 | 7/2006 | Motsenbocker et al. |
| 7,097,659 B2 | 8/2006 | Woolfson et al. |
| 7,105,016 B2 | 9/2006 | Shiu et al. |
| 7,115,141 B2 | 10/2006 | Menz et al. |
| 7,125,418 B2 | 10/2006 | Duran et al. |
| 7,128,759 B2 | 10/2006 | Osborne et al. |
| 7,147,663 B1 | 12/2006 | Berg et al. |
| 7,153,324 B2 | 12/2006 | Case et al. |
| 7,160,319 B2 | 1/2007 | Chouinard et al. |
| 7,175,656 B2 | 2/2007 | Khairkhahan |
| 7,186,265 B2 | 3/2007 | Sharkawy et al. |
| 7,195,641 B2 | 3/2007 | Palmaz et al. |
| 7,198,646 B2 | 4/2007 | Figulla et al. |
| 7,201,761 B2 | 4/2007 | Woolfson et al. |
| 7,201,772 B2 | 4/2007 | Schwammenthal et al. |
| 7,211,107 B2 | 5/2007 | Bruckheime et al. |
| 7,252,682 B2 | 8/2007 | Seguin |
| 7,255,706 B2 | 8/2007 | Rosengart |
| 7,258,698 B2 | 8/2007 | Lemmon |
| 7,261,732 B2 | 8/2007 | Justino |
| 7,276,078 B2 | 10/2007 | Spenser et al. |
| 7,300,457 B2 | 11/2007 | Palmaz |
| 7,300,463 B2 | 11/2007 | Liddicoat |
| 7,316,706 B2 | 1/2008 | Bloom et al. |
| 7,329,278 B2 | 2/2008 | Seguin et al. |
| 7,329,279 B2 | 2/2008 | Haug et al. |
| 7,335,218 B2 | 2/2008 | Wilson et al. |
| 7,338,484 B2 | 3/2008 | Schoon et al. |
| 7,338,520 B2 | 3/2008 | Bailey et al. |
| 7,347,869 B2 | 3/2008 | Hojeibane et al. |
| 7,351,256 B2 | 4/2008 | Hojeibane et al. |
| 7,357,814 B2 | 4/2008 | Gabbay |
| 7,367,984 B2 | 5/2008 | Kulcinski et al. |
| 7,374,571 B2 | 5/2008 | Pease et al. |
| 7,377,938 B2 | 5/2008 | Sarac et al. |
| 7,377,941 B2 | 5/2008 | Rhee et al. |
| 7,381,218 B2 | 6/2008 | Schreck |
| 7,384,411 B1 | 6/2008 | Condado |
| 7,393,360 B2 | 7/2008 | Spenser et al. |
| 7,427,291 B2 | 9/2008 | Liddicoat et al. |
| 7,429,269 B2 | 9/2008 | Schwammenthal et al. |
| 7,442,204 B2 | 10/2008 | Schwammenthal et al. |
| 7,453,227 B2 | 11/2008 | Prisco et al. |
| 7,455,690 B2 | 11/2008 | Cartledge et al. |
| 7,462,191 B2 | 12/2008 | Spenser et al. |
| 7,470,284 B2 | 12/2008 | Lambrecht et al. |
| 7,481,838 B2 | 1/2009 | Carpentier et al. |
| 7,534,259 B2 | 5/2009 | Lashinski et al. |
| 7,544,206 B2 | 6/2009 | Cohn |
| 7,547,322 B2 | 6/2009 | Sarac et al. |
| 7,556,645 B2 | 7/2009 | Lashinski et al. |
| 7,556,646 B2 | 7/2009 | Yang et al. |
| 7,569,071 B2 | 8/2009 | Haverkost et al. |
| 7,578,843 B2 | 8/2009 | Shu |
| 7,585,321 B2 | 9/2009 | Cribier |
| 7,591,848 B2 | 9/2009 | Allen |
| 7,618,446 B2 | 11/2009 | Andersen et al. |
| 7,618,447 B2 | 11/2009 | Case et al. |
| 7,682,390 B2 | 3/2010 | Seguin |
| 7,708,775 B2 | 5/2010 | Rowe et al. |
| 7,780,726 B2 | 8/2010 | Seguin |
| 7,785,341 B2 | 8/2010 | Forster et al. |
| 7,806,919 B2 | 10/2010 | Bloom et al. |
| 7,857,845 B2 | 12/2010 | Stacchino et al. |
| 7,972,378 B2 | 7/2011 | Tabor et al. |
| 7,981,153 B2 | 7/2011 | Fogarty et al. |
| 8,006,535 B2 | 8/2011 | Righini et al. |
| 8,043,360 B2 | 10/2011 | McNamara et al. |
| 8,083,793 B2 | 12/2011 | Lane et al. |
| 8,109,996 B2 | 2/2012 | Stacchino et al. |
| 8,211,169 B2 | 7/2012 | Lane et al. |
| 8,535,373 B2 | 9/2013 | Stacchino et al. |
| 8,539,662 B2 | 9/2013 | Stacchino et al. |
| 8,540,768 B2 | 9/2013 | Stacchino et al. |
| 8,834,563 B2 | 9/2014 | Righini |
| 8,920,492 B2 | 12/2014 | Stacchino et al. |
| 9,161,836 B2 | 10/2015 | Rolando et al. |
| 9,248,017 B2 | 2/2016 | Rolando et al. |
| 9,289,289 B2 | 3/2016 | Rolando et al. |
| 2001/0001314 A1 | 5/2001 | Davison et al. |
| 2001/0002445 A1 | 5/2001 | Vesely |
| 2001/0007956 A1 | 7/2001 | Letac et al. |
| 2001/0010017 A1 | 7/2001 | Letac et al. |
| 2001/0011189 A1 | 8/2001 | Drasler et al. |
| 2001/0021872 A1 | 9/2001 | Bailey et al. |
| 2001/0025196 A1 | 9/2001 | Chinn et al. |
| 2001/0032013 A1 | 10/2001 | Marton |
| 2001/0039450 A1 | 11/2001 | Pavcnik et al. |
| 2001/0041928 A1 | 11/2001 | Pavcnik et al. |
| 2001/0044647 A1 | 11/2001 | Pinchuk et al. |
| 2001/0049558 A1 | 12/2001 | Liddicoat et al. |

(56) References Cited

U.S. PATENT DOCUMENTS

| | | |
|---|---|---|
| 2002/0010508 A1 | 1/2002 | Chobotov |
| 2002/0029014 A1 | 3/2002 | Jayaraman |
| 2002/0029783 A1 | 3/2002 | Stevens et al. |
| 2002/0032480 A1 | 3/2002 | Spence et al. |
| 2002/0032481 A1 | 3/2002 | Gabbay |
| 2002/0035390 A1 | 3/2002 | Schaldach et al. |
| 2002/0035396 A1 | 3/2002 | Heath |
| 2002/0042650 A1 | 4/2002 | Vardi et al. |
| 2002/0042651 A1 | 4/2002 | Liddicoat et al. |
| 2002/0058994 A1 | 5/2002 | Hill et al. |
| 2002/0058995 A1 | 5/2002 | Stevens |
| 2002/0072789 A1 | 6/2002 | Hackett et al. |
| 2002/0095209 A1 | 7/2002 | Zadno Azizi et al. |
| 2002/0103533 A1 | 8/2002 | Langberg et al. |
| 2002/0107565 A1 | 8/2002 | Greenhalgh |
| 2002/0111674 A1 | 8/2002 | Chouinard et al. |
| 2002/0123802 A1 | 9/2002 | Snyders |
| 2002/0128702 A1 | 9/2002 | Menz et al. |
| 2002/0129820 A1 | 9/2002 | Ryan et al. |
| 2002/0133183 A1 | 9/2002 | Lentz et al. |
| 2002/0133226 A1 | 9/2002 | Marquez et al. |
| 2002/0138138 A1 | 9/2002 | Yang |
| 2002/0151970 A1* | 10/2002 | Garrison ............... A61F 2/2418 623/2.11 |
| 2002/0161377 A1 | 10/2002 | Rabkin |
| 2002/0161392 A1 | 10/2002 | Dubrul |
| 2002/0161394 A1 | 10/2002 | Macoviak et al. |
| 2002/0183839 A1 | 12/2002 | Garrison et al. |
| 2002/0193871 A1 | 12/2002 | Beyersdorf et al. |
| 2002/0198594 A1 | 12/2002 | Schreck |
| 2003/0014104 A1 | 1/2003 | Cribier |
| 2003/0023300 A1 | 1/2003 | Bailey et al. |
| 2003/0023303 A1 | 1/2003 | Palmaz et al. |
| 2003/0028247 A1 | 2/2003 | Cali |
| 2003/0036791 A1 | 2/2003 | Philipp et al. |
| 2003/0036795 A1 | 2/2003 | Andersen et al. |
| 2003/0040771 A1 | 2/2003 | Hyodoh et al. |
| 2003/0040772 A1 | 2/2003 | Hyodoh et al. |
| 2003/0050694 A1 | 3/2003 | Yang et al. |
| 2003/0055495 A1 | 3/2003 | Pease et al. |
| 2003/0065386 A1 | 4/2003 | Weadock |
| 2003/0069492 A1 | 4/2003 | Abrams et al. |
| 2003/0109924 A1 | 6/2003 | Cribier |
| 2003/0114913 A1 | 6/2003 | Spenser et al. |
| 2003/0125795 A1 | 7/2003 | Pavcnik et al. |
| 2003/0125805 A1 | 7/2003 | Johnson et al. |
| 2003/0130726 A1 | 7/2003 | Thorpe et al. |
| 2003/0130729 A1 | 7/2003 | Paniagua et al. |
| 2003/0139804 A1 | 7/2003 | Hankh et al. |
| 2003/0149475 A1 | 8/2003 | Hyodoh et al. |
| 2003/0149476 A1 | 8/2003 | Damm et al. |
| 2003/0149478 A1 | 8/2003 | Figulla et al. |
| 2003/0153974 A1 | 8/2003 | Spenser et al. |
| 2003/0163194 A1 | 8/2003 | Quijano et al. |
| 2003/0181850 A1 | 9/2003 | Diamond et al. |
| 2003/0191519 A1 | 10/2003 | Lombardi et al. |
| 2003/0191528 A1 | 10/2003 | Quijano et al. |
| 2003/0192164 A1 | 10/2003 | Austin |
| 2003/0199913 A1 | 10/2003 | Dubrul et al. |
| 2003/0199963 A1 | 10/2003 | Tower et al. |
| 2003/0208261 A1 | 11/2003 | Thorpe et al. |
| 2003/0212410 A1 | 11/2003 | Stenzel et al. |
| 2003/0212454 A1 | 11/2003 | Scott et al. |
| 2003/0225445 A1 | 12/2003 | Derus et al. |
| 2004/0019374 A1 | 1/2004 | Hojeibane et al. |
| 2004/0034407 A1 | 2/2004 | Sherry |
| 2004/0034411 A1 | 2/2004 | Quijano et al. |
| 2004/0039436 A1 | 2/2004 | Spenser et al. |
| 2004/0049224 A1 | 3/2004 | Buehlmann et al. |
| 2004/0049262 A1 | 3/2004 | Obermiller et al. |
| 2004/0049266 A1 | 3/2004 | Anduiza et al. |
| 2004/0055606 A1 | 3/2004 | Hendricksen et al. |
| 2004/0073301 A1 | 4/2004 | Donlon et al. |
| 2004/0078072 A1 | 4/2004 | Tu et al. |
| 2004/0078074 A1 | 4/2004 | Anderson et al. |
| 2004/0082904 A1 | 4/2004 | Houde et al. |
| 2004/0088045 A1 | 5/2004 | Cox |
| 2004/0092858 A1 | 5/2004 | Wilson et al. |
| 2004/0092989 A1 | 5/2004 | Wilson et al. |
| 2004/0093005 A1 | 5/2004 | Durcan |
| 2004/0093060 A1 | 5/2004 | Seguin et al. |
| 2004/0093070 A1 | 5/2004 | Hojeibane et al. |
| 2004/0093075 A1 | 5/2004 | Kuehne |
| 2004/0097788 A1 | 5/2004 | Mourlas et al. |
| 2004/0098112 A1 | 5/2004 | DiMatteo et al. |
| 2004/0106976 A1 | 6/2004 | Bailey et al. |
| 2004/0106990 A1 | 6/2004 | Spence et al. |
| 2004/0111096 A1 | 6/2004 | Tu et al. |
| 2004/0116951 A1 | 6/2004 | Rosengart |
| 2004/0117004 A1 | 6/2004 | Osborne et al. |
| 2004/0122468 A1 | 6/2004 | Yodfat et al. |
| 2004/0122514 A1 | 6/2004 | Fogarty et al. |
| 2004/0122516 A1 | 6/2004 | Fogarty et al. |
| 2004/0123437 A1 | 7/2004 | Kokish |
| 2004/0127979 A1 | 7/2004 | Wilson et al. |
| 2004/0138742 A1 | 7/2004 | Myers et al. |
| 2004/0138743 A1 | 7/2004 | Myers et al. |
| 2004/0153146 A1 | 8/2004 | Lashinski et al. |
| 2004/0167573 A1 | 8/2004 | Williamson et al. |
| 2004/0167620 A1 | 8/2004 | Ortiz et al. |
| 2004/0186558 A1 | 9/2004 | Pavcnik et al. |
| 2004/0186563 A1 | 9/2004 | Lobbi |
| 2004/0193259 A1 | 9/2004 | Gabbay |
| 2004/0193261 A1 | 9/2004 | Berreklouw |
| 2004/0210240 A1 | 10/2004 | Saint |
| 2004/0210304 A1 | 10/2004 | Seguin et al. |
| 2004/0210307 A1 | 10/2004 | Khairkhahan |
| 2004/0215333 A1 | 10/2004 | Duran et al. |
| 2004/0215339 A1 | 10/2004 | Drasler et al. |
| 2004/0225353 A1 | 11/2004 | McGuckin et al. |
| 2004/0225354 A1 | 11/2004 | Allen et al. |
| 2004/0225355 A1 | 11/2004 | Stevens |
| 2004/0225356 A1 | 11/2004 | Frater |
| 2004/0254636 A1 | 12/2004 | Flagle et al. |
| 2004/0260389 A1 | 12/2004 | Case et al. |
| 2004/0260394 A1 | 12/2004 | Douk et al. |
| 2004/0267357 A1 | 12/2004 | Allen et al. |
| 2005/0010246 A1 | 1/2005 | Streeter et al. |
| 2005/0010285 A1 | 1/2005 | Lambrecht et al. |
| 2005/0010287 A1 | 1/2005 | Macoviak et al. |
| 2005/0015112 A1 | 1/2005 | Cohn et al. |
| 2005/0027348 A1 | 2/2005 | Case et al. |
| 2005/0033398 A1 | 2/2005 | Seguin |
| 2005/0043790 A1 | 2/2005 | Seguin |
| 2005/0049692 A1 | 3/2005 | Numamoto et al. |
| 2005/0049696 A1 | 3/2005 | Siess et al. |
| 2005/0055088 A1 | 3/2005 | Liddicoat et al. |
| 2005/0060029 A1 | 3/2005 | Le et al. |
| 2005/0060030 A1 | 3/2005 | Lashinski et al. |
| 2005/0075584 A1 | 4/2005 | Cali |
| 2005/0075712 A1 | 4/2005 | Biancucci et al. |
| 2005/0075713 A1 | 4/2005 | Biancucci et al. |
| 2005/0075717 A1 | 4/2005 | Nguyen et al. |
| 2005/0075718 A1 | 4/2005 | Nguyen et al. |
| 2005/0075719 A1 | 4/2005 | Bergheim |
| 2005/0075720 A1* | 4/2005 | Nguyen ............... A61F 2/2418 623/1.26 |
| 2005/0075724 A1 | 4/2005 | Svanidze et al. |
| 2005/0075726 A1 | 4/2005 | Svanidze et al. |
| 2005/0075727 A1 | 4/2005 | Wheatley |
| 2005/0075728 A1 | 4/2005 | Nguyen et al. |
| 2005/0075729 A1 | 4/2005 | Nguyen et al. |
| 2005/0075730 A1 | 4/2005 | Myers et al. |
| 2005/0075731 A1 | 4/2005 | Artof et al. |
| 2005/0085841 A1 | 4/2005 | Eversull et al. |
| 2005/0085842 A1 | 4/2005 | Eversull et al. |
| 2005/0085843 A1 | 4/2005 | Opolski et al. |
| 2005/0085890 A1 | 4/2005 | Rasmussen et al. |
| 2005/0085900 A1 | 4/2005 | Case et al. |
| 2005/0096568 A1 | 5/2005 | Kato |
| 2005/0096692 A1 | 5/2005 | Linder et al. |
| 2005/0096724 A1 | 5/2005 | Stenzel et al. |
| 2005/0096734 A1 | 5/2005 | Majercak et al. |
| 2005/0096735 A1 | 5/2005 | Hojeibane et al. |

(56) References Cited

U.S. PATENT DOCUMENTS

| | | |
|---|---|---|
| 2005/0096736 A1 | 5/2005 | Osse et al. |
| 2005/0107871 A1 | 5/2005 | Realyvasquez et al. |
| 2005/0113910 A1 | 5/2005 | Paniagua et al. |
| 2005/0119688 A1 | 6/2005 | Bergheim |
| 2005/0131438 A1 | 6/2005 | Cohn |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137692 A1 | 6/2005 | Haug et al. |
| 2005/0137693 A1 | 6/2005 | Haug et al. |
| 2005/0137694 A1 | 6/2005 | Haug et al. |
| 2005/0137695 A1 | 6/2005 | Salahieh et al. |
| 2005/0137696 A1 | 6/2005 | Salahieh et al. |
| 2005/0137697 A1 | 6/2005 | Salahieh et al. |
| 2005/0137698 A1 | 6/2005 | Salahieh et al. |
| 2005/0137699 A1 | 6/2005 | Salahieh et al. |
| 2005/0137701 A1 | 6/2005 | Salahieh et al. |
| 2005/0137702 A1 | 6/2005 | Haug et al. |
| 2005/0143807 A1 | 6/2005 | Pavcnik et al. |
| 2005/0143809 A1 | 6/2005 | Salahieh et al. |
| 2005/0148997 A1 | 7/2005 | Valley et al. |
| 2005/0149181 A1 | 7/2005 | Eberhardt |
| 2005/0165477 A1 | 7/2005 | Anduiza et al. |
| 2005/0166389 A1 | 8/2005 | Perreault et al. |
| 2005/0187616 A1 | 8/2005 | Realyvasquez |
| 2005/0197695 A1 | 9/2005 | Stacchino et al. |
| 2005/0197696 A1 | 9/2005 | Gomez Duran |
| 2005/0203549 A1 | 9/2005 | Realyvasquez |
| 2005/0203605 A1 | 9/2005 | Dolan |
| 2005/0203618 A1 | 9/2005 | Sharkawy et al. |
| 2005/0222674 A1 | 10/2005 | Paine |
| 2005/0222675 A1 | 10/2005 | Sauter |
| 2005/0228495 A1 | 10/2005 | Macoviak |
| 2005/0229670 A1 | 10/2005 | Perreault |
| 2005/0234537 A1 | 10/2005 | Edin |
| 2005/0234546 A1 | 10/2005 | Nugent et al. |
| 2005/0240200 A1 | 10/2005 | Bergheim |
| 2005/0240256 A1 | 10/2005 | Austin |
| 2005/0240263 A1 | 10/2005 | Fogarty et al. |
| 2005/0261759 A1 | 11/2005 | Lambrecht et al. |
| 2005/0267529 A1 | 12/2005 | Crockett et al. |
| 2005/0283232 A1 | 12/2005 | Gabbay |
| 2005/0283962 A1 | 12/2005 | Boudjemline |
| 2006/0004439 A1 | 1/2006 | Spenser et al. |
| 2006/0004442 A1 | 1/2006 | Spenser et al. |
| 2006/0004469 A1 | 1/2006 | Sokel |
| 2006/0009841 A1 | 1/2006 | McGuckin et al. |
| 2006/0025855 A1 | 2/2006 | Lashinski et al. |
| 2006/0052867 A1 | 3/2006 | Revuelta et al. |
| 2006/0058775 A1 | 3/2006 | Stevens et al. |
| 2006/0058872 A1 | 3/2006 | Salahieh et al. |
| 2006/0074486 A1 | 4/2006 | Liddicoat et al. |
| 2006/0085060 A1 | 4/2006 | Campbell |
| 2006/0089711 A1 | 4/2006 | Dolan |
| 2006/0095117 A1 | 5/2006 | Popelar et al. |
| 2006/0100685 A1 | 5/2006 | Seguin et al. |
| 2006/0116757 A1 | 6/2006 | Lashinski et al. |
| 2006/0135964 A1 | 6/2006 | Vesely |
| 2006/0142848 A1 | 6/2006 | Gabbay |
| 2006/0167474 A1 | 7/2006 | Bloom et al. |
| 2006/0178740 A1 | 8/2006 | Stacchino et al. |
| 2006/0190017 A1 | 8/2006 | Cyr et al. |
| 2006/0195134 A1 | 8/2006 | Crittenden |
| 2006/0195184 A1 | 8/2006 | Lane et al. |
| 2006/0206192 A1 | 9/2006 | Tower et al. |
| 2006/0206202 A1 | 9/2006 | Bonhoeffer et al. |
| 2006/0212111 A1 | 9/2006 | Case et al. |
| 2006/0247763 A1 | 11/2006 | Slater |
| 2006/0253134 A1 | 11/2006 | Ortiz et al. |
| 2006/0259134 A1 | 11/2006 | Schwammenthal et al. |
| 2006/0259136 A1 | 11/2006 | Nguyen et al. |
| 2006/0259137 A1 | 11/2006 | Artof et al. |
| 2006/0265056 A1 | 11/2006 | Nguyen et al. |
| 2006/0265855 A1 | 11/2006 | Stenzel |
| 2006/0271166 A1 | 11/2006 | Thill et al. |
| 2006/0271175 A1 | 11/2006 | Woolfson et al. |
| 2006/0276874 A1 | 12/2006 | Wilson et al. |
| 2006/0276882 A1 | 12/2006 | Case et al. |
| 2006/0282161 A1 | 12/2006 | Huynh et al. |
| 2007/0005129 A1 | 1/2007 | Damm et al. |
| 2007/0005131 A1 | 1/2007 | Taylor |
| 2007/0010878 A1 | 1/2007 | Rafiee et al. |
| 2007/0016286 A1 | 1/2007 | Herrmann et al. |
| 2007/0027518 A1 | 2/2007 | Case et al. |
| 2007/0027533 A1 | 2/2007 | Douk |
| 2007/0027534 A1 | 2/2007 | Bergheim et al. |
| 2007/0032850 A1 | 2/2007 | Ruiz et al. |
| 2007/0038295 A1 | 2/2007 | Case et al. |
| 2007/0043431 A1 | 2/2007 | Melsheimer |
| 2007/0043435 A1 | 2/2007 | Seguin et al. |
| 2007/0051377 A1 | 3/2007 | Douk et al. |
| 2007/0056346 A1 | 3/2007 | Spenser et al. |
| 2007/0061009 A1 | 3/2007 | Spenser et al. |
| 2007/0073387 A1 | 3/2007 | Forster et al. |
| 2007/0073392 A1 | 3/2007 | Heyninck Jantz et al. |
| 2007/0078509 A1 | 4/2007 | Lotfy |
| 2007/0078510 A1 | 4/2007 | Ryan |
| 2007/0088431 A1 | 4/2007 | Bourang et al. |
| 2007/0093869 A1 | 4/2007 | Bloom et al. |
| 2007/0093887 A1 | 4/2007 | Case et al. |
| 2007/0093890 A1 | 4/2007 | Eliasen et al. |
| 2007/0100356 A1 | 5/2007 | Lucatero et al. |
| 2007/0100432 A1 | 5/2007 | Case et al. |
| 2007/0100435 A1 | 5/2007 | Case et al. |
| 2007/0100439 A1 | 5/2007 | Cangialosi et al. |
| 2007/0100440 A1 | 5/2007 | Figulla et al. |
| 2007/0100449 A1 | 5/2007 | O'Neil et al. |
| 2007/0106372 A1 | 5/2007 | Osborne et al. |
| 2007/0112415 A1 | 5/2007 | Bartlett |
| 2007/0112422 A1 | 5/2007 | Dehdashtian |
| 2007/0118209 A1 | 5/2007 | Strecker |
| 2007/0118215 A1 | 5/2007 | Moaddeb |
| 2007/0142968 A1 | 6/2007 | Prisco et al. |
| 2007/0162102 A1 | 7/2007 | Ryan et al. |
| 2007/0162113 A1 | 7/2007 | Sharkawy et al. |
| 2007/0168024 A1 | 7/2007 | Khairkhahan |
| 2007/0173861 A1 | 7/2007 | Strommer et al. |
| 2007/0185513 A1 | 8/2007 | Woolfson et al. |
| 2007/0203391 A1 | 8/2007 | Bloom et al. |
| 2007/0203503 A1 | 8/2007 | Salahieh et al. |
| 2007/0225681 A1 | 9/2007 | House |
| 2007/0232898 A1 | 10/2007 | Huynh et al. |
| 2007/0233228 A1 | 10/2007 | Eberhardt et al. |
| 2007/0233237 A1 | 10/2007 | Krivoruchko |
| 2007/0233238 A1 | 10/2007 | Huynh et al. |
| 2007/0237802 A1 | 10/2007 | McKay |
| 2007/0238979 A1 | 10/2007 | Huynh et al. |
| 2007/0239254 A1 | 10/2007 | Chia et al. |
| 2007/0239265 A1 | 10/2007 | Birdsall |
| 2007/0239266 A1 | 10/2007 | Birdsall |
| 2007/0239269 A1 | 10/2007 | Dolan et al. |
| 2007/0239271 A1 | 10/2007 | Nguyen |
| 2007/0239273 A1 | 10/2007 | Allen |
| 2007/0244544 A1 | 10/2007 | Birdsall et al. |
| 2007/0244545 A1 | 10/2007 | Birdsall et al. |
| 2007/0244546 A1 | 10/2007 | Francis |
| 2007/0244553 A1 | 10/2007 | Rafiee et al. |
| 2007/0244554 A1 | 10/2007 | Rafiee et al. |
| 2007/0244555 A1 | 10/2007 | Rafiee et al. |
| 2007/0244556 A1 | 10/2007 | Rafiee et al. |
| 2007/0244557 A1 | 10/2007 | Rafiee et al. |
| 2007/0250160 A1 | 10/2007 | Rafiee |
| 2007/0255394 A1 | 11/2007 | Ryan |
| 2007/0255396 A1 | 11/2007 | Douk et al. |
| 2007/0260305 A1 | 11/2007 | Drews et al. |
| 2007/0265701 A1 | 11/2007 | Gurskis et al. |
| 2007/0270944 A1 | 11/2007 | Bergheim et al. |
| 2007/0288000 A1 | 12/2007 | Bonan |
| 2007/0293942 A1 | 12/2007 | Mirzaee |
| 2008/0004696 A1 | 1/2008 | Vesely |
| 2008/0009940 A1 | 1/2008 | Cribier |

(56) References Cited

U.S. PATENT DOCUMENTS

| | | |
|---|---|---|
| 2008/0015671 A1 | 1/2008 | Bonhoeffer |
| 2008/0021552 A1 | 1/2008 | Gabbay |
| 2008/0048656 A1 | 2/2008 | Tan et al. |
| 2008/0065001 A1 | 3/2008 | DiNucci et al. |
| 2008/0065204 A1 | 3/2008 | Macoviak et al. |
| 2008/0065206 A1 | 3/2008 | Liddicoat |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0071369 A1 | 3/2008 | Tuval et al. |
| 2008/0077234 A1 | 3/2008 | Styrc |
| 2008/0082164 A1 | 4/2008 | Friedman |
| 2008/0082165 A1 | 4/2008 | Wilson et al. |
| 2008/0082166 A1 | 4/2008 | Styrc et al. |
| 2008/0097595 A1 | 4/2008 | Gabbay |
| 2008/0103586 A1 | 5/2008 | Styrc et al. |
| 2008/0125859 A1 | 5/2008 | Salahieh et al. |
| 2008/0133033 A1 | 6/2008 | Wolff et al. |
| 2008/0140189 A1 | 6/2008 | Nguyen et al. |
| 2008/0147105 A1 | 6/2008 | Wilson et al. |
| 2008/0147160 A1 | 6/2008 | Ghione et al. |
| 2008/0147180 A1 | 6/2008 | Ghione et al. |
| 2008/0147181 A1 | 6/2008 | Ghione et al. |
| 2008/0147182 A1 | 6/2008 | Righini et al. |
| 2008/0154355 A1 | 6/2008 | Benichou et al. |
| 2008/0154356 A1 | 6/2008 | Obermiller et al. |
| 2008/0161910 A1 | 7/2008 | Revuelta et al. |
| 2008/0161911 A1 | 7/2008 | Revuelta et al. |
| 2008/0183273 A1 | 7/2008 | Mesana et al. |
| 2008/0188880 A1 | 8/2008 | Fischer et al. |
| 2008/0188928 A1 | 8/2008 | Salahieh et al. |
| 2008/0215143 A1 | 9/2008 | Seguin |
| 2008/0215144 A1 | 9/2008 | Ryan et al. |
| 2008/0228254 A1 | 9/2008 | Ryan |
| 2008/0228263 A1 | 9/2008 | Ryan |
| 2008/0234797 A1 | 9/2008 | Styrc |
| 2008/0243246 A1 | 10/2008 | Ryan et al. |
| 2008/0249619 A1 | 10/2008 | Stacchino et al. |
| 2008/0255651 A1 | 10/2008 | Dwork |
| 2008/0255660 A1 | 10/2008 | Guyenot et al. |
| 2008/0255661 A1 | 10/2008 | Straubinger et al. |
| 2008/0255662 A1 | 10/2008 | Stacchino et al. |
| 2008/0262593 A1 | 10/2008 | Ryan et al. |
| 2008/0262603 A1 | 10/2008 | Giaquinta et al. |
| 2008/0269878 A1 | 10/2008 | Iobbi |
| 2009/0005863 A1 | 1/2009 | Goetz et al. |
| 2009/0012600 A1 | 1/2009 | Styrc et al. |
| 2009/0018570 A1 | 1/2009 | Righini et al. |
| 2009/0048656 A1 | 2/2009 | Wen |
| 2009/0054976 A1 | 2/2009 | Tuval et al. |
| 2009/0069886 A1 | 3/2009 | Suri et al. |
| 2009/0069887 A1 | 3/2009 | Righini et al. |
| 2009/0069889 A1 | 3/2009 | Suri et al. |
| 2009/0082858 A1 | 3/2009 | Nugent et al. |
| 2009/0085900 A1 | 4/2009 | Weiner |
| 2009/0099653 A1 | 4/2009 | Suri et al. |
| 2009/0138079 A1 | 5/2009 | Tuval et al. |
| 2009/0157175 A1 | 6/2009 | Benichou |
| 2009/0164004 A1 | 6/2009 | Cohn |
| 2009/0164006 A1 | 6/2009 | Seguin et al. |
| 2009/0171447 A1 | 7/2009 | Von Segesser et al. |
| 2009/0171456 A1 | 7/2009 | Kveen et al. |
| 2009/0192585 A1 | 7/2009 | Bloom et al. |
| 2009/0192586 A1 | 7/2009 | Tabor et al. |
| 2009/0192591 A1 | 7/2009 | Ryan et al. |
| 2009/0192603 A1 | 7/2009 | Ryan |
| 2009/0198316 A1 | 8/2009 | Laske et al. |
| 2009/0209955 A1 | 8/2009 | Forster et al. |
| 2009/0210025 A1 | 8/2009 | Ameri |
| 2009/0210052 A1 | 8/2009 | Forster et al. |
| 2009/0216310 A1 | 8/2009 | Straubinger et al. |
| 2009/0216312 A1 | 8/2009 | Straubinger et al. |
| 2009/0216313 A1 | 8/2009 | Straubinger et al. |
| 2009/0222082 A1 | 9/2009 | Lock et al. |
| 2009/0222084 A1 | 9/2009 | Friedman |
| 2009/0234443 A1 | 9/2009 | Ottma et al. |
| 2009/0240264 A1 | 9/2009 | Tuval et al. |
| 2009/0240320 A1 | 9/2009 | Tuval et al. |
| 2009/0254165 A1 | 10/2009 | Tabor et al. |
| 2009/0287296 A1 | 11/2009 | Manasse |
| 2009/0287299 A1 | 11/2009 | Tabor et al. |
| 2010/0004740 A1 | 1/2010 | Seguin et al. |
| 2010/0030328 A1 | 2/2010 | Seguin et al. |
| 2010/0036479 A1 | 2/2010 | Hill et al. |
| 2010/0036485 A1 | 2/2010 | Seguin |
| 2010/0069852 A1 | 3/2010 | Kelley |
| 2010/0094411 A1 | 4/2010 | Tuval et al. |
| 2010/0100167 A1 | 4/2010 | Bortlein et al. |
| 2010/0131054 A1 | 5/2010 | Tuval et al. |
| 2010/0137979 A1 | 6/2010 | Tuval et al. |
| 2010/0145439 A1 | 6/2010 | Seguin et al. |
| 2010/0152840 A1 | 6/2010 | Seguin et al. |
| 2010/0161045 A1 | 6/2010 | Righini |
| 2010/0198346 A1 | 8/2010 | Keogh et al. |
| 2010/0234940 A1 | 9/2010 | Dolan |
| 2010/0249661 A1 | 9/2010 | Righini et al. |
| 2010/0256723 A1 | 10/2010 | Murray |
| 2010/0262043 A1 | 10/2010 | Sauter et al. |
| 2010/0274351 A1 | 10/2010 | Rolando et al. |
| 2010/0292782 A1 | 11/2010 | Giannetti et al. |
| 2011/0082539 A1 | 4/2011 | Suri |
| 2011/0288636 A1 | 11/2011 | Rolando et al. |
| 2012/0172982 A1 | 7/2012 | Stacchino et al. |
| 2013/0172991 A1 | 7/2013 | Rolando et al. |
| 2013/0345800 A1 | 12/2013 | Stacchino et al. |
| 2014/0052243 A1 | 2/2014 | Rolando et al. |
| 2014/0052244 A1 | 2/2014 | Rolando et al. |
| 2014/0350666 A1 | 11/2014 | Righini |
| 2015/0148895 A1 | 5/2015 | Stacchino et al. |

FOREIGN PATENT DOCUMENTS

| | | |
|---|---|---|
| DE | 19532846 A1 | 3/1997 |
| DE | 19546692 C2 | 6/1997 |
| DE | 29911694 U1 | 9/1999 |
| DE | 19907646 A1 | 8/2000 |
| DE | 10010074 A1 | 10/2001 |
| DE | 10049812 A1 | 4/2002 |
| DE | 10049813 C1 | 4/2002 |
| DE | 10049815 A1 | 4/2002 |
| DE | 10121210 A1 | 11/2002 |
| DE | 10301026 A1 | 2/2004 |
| DE | 19857887 A1 | 5/2005 |
| DE | 102004019254 B3 | 11/2005 |
| EP | 0133420 B1 | 2/1988 |
| EP | 0155245 B1 | 5/1990 |
| EP | 0401199 B1 | 1/1995 |
| EP | 0592410 B1 | 10/1995 |
| EP | 0515324 B1 | 12/1996 |
| EP | 0850607 A1 | 7/1998 |
| EP | 1057460 A1 | 12/2000 |
| EP | 0778009 B1 | 7/2002 |
| EP | 1259194 B1 | 2/2005 |
| EP | 1214020 B1 | 3/2005 |
| EP | 1353420 B1 | 3/2005 |
| EP | 1088529 B1 | 6/2005 |
| EP | 1014896 B1 | 11/2005 |
| EP | 1469797 A1 | 11/2005 |
| EP | 1603493 A2 | 12/2005 |
| EP | 1174098 B1 | 3/2006 |
| EP | 1600127 B1 | 11/2006 |
| EP | 1255510 A1 | 4/2007 |
| EP | 1143882 B1 | 12/2007 |
| EP | 1913901 A1 | 4/2008 |
| EP | 1690515 B1 | 7/2008 |
| EP | 1570809 B1 | 1/2009 |
| EP | 1330213 B1 | 3/2009 |
| EP | 2047824 A1 | 4/2009 |
| EP | 2055266 A2 | 5/2009 |
| EP | 1370201 B1 | 9/2009 |
| EP | 2119417 A2 | 11/2009 |
| EP | 2133039 A2 | 12/2009 |

(56) References Cited

FOREIGN PATENT DOCUMENTS

| | | |
|---|---|---|
| EP | 2246011 A1 | 3/2010 |
| FR | 2788217 A1 | 7/2000 |
| FR | 2815844 A1 | 1/2003 |
| GB | 2083362 A | 3/1982 |
| GB | 2056023 A | 8/1983 |
| GB | 2433700 A | 12/2007 |
| JP | 11332997 A | 12/1999 |
| NL | 1017275 C2 | 8/2002 |
| SU | 1271508 A1 | 11/1986 |
| WO | WO9209247 A1 | 6/1992 |
| WO | WO1995029640 A1 | 11/1995 |
| WO | WO1996039942 A1 | 12/1996 |
| WO | WO1997024989 A1 | 7/1997 |
| WO | WO1998014138 A1 | 4/1998 |
| WO | WO1998017202 A1 | 4/1998 |
| WO | WO1998029057 A1 | 7/1998 |
| WO | WO1999013802 A1 | 3/1999 |
| WO | WO1999053864 A1 | 10/1999 |
| WO | WO1999055255 A1 | 11/1999 |
| WO | WO1999056665 A1 | 11/1999 |
| WO | WO1999053866 A1 | 2/2000 |
| WO | WO2000006052 A1 | 2/2000 |
| WO | WO2000021464 A1 | 4/2000 |
| WO | WO2000030565 A1 | 6/2000 |
| WO | WO2000041652 A1 | 7/2000 |
| WO | WO2000044313 A1 | 8/2000 |
| WO | WO2000047136 A1 | 8/2000 |
| WO | WO2000047139 A1 | 8/2000 |
| WO | WO2000062714 A1 | 10/2000 |
| WO | WO2000062716 A1 | 10/2000 |
| WO | WO2001021076 A1 | 3/2001 |
| WO | WO2001021107 A1 | 3/2001 |
| WO | WO2001035870 A1 | 5/2001 |
| WO | WO2001049213 A2 | 7/2001 |
| WO | WO2001054625 A1 | 8/2001 |
| WO | WO2001062189 A1 | 8/2001 |
| WO | WO2001064137 A1 | 9/2001 |
| WO | WO2001076510 A2 | 10/2001 |
| WO | WO2002011646 A1 | 2/2002 |
| WO | WO2002022054 A1 | 3/2002 |
| WO | WO2002036048 A1 | 5/2002 |
| WO | WO2001021110 A1 | 8/2002 |
| WO | WO2002041789 A2 | 8/2002 |
| WO | WO2001021103 A2 | 10/2002 |
| WO | WO2002076348 A1 | 10/2002 |
| WO | WO2002092257 A1 | 11/2002 |
| WO | WO2002047575 A2 | 12/2002 |
| WO | WO2003011195 A2 | 2/2003 |
| WO | WO2003047468 A1 | 6/2003 |
| WO | WO2003003943 A2 | 11/2003 |
| WO | WO2003094797 A1 | 11/2003 |
| WO | WO2003003949 A2 | 1/2004 |
| WO | WO2004019825 A1 | 3/2004 |
| WO | WO2004082527 A2 | 9/2004 |
| WO | WO2004089250 A1 | 10/2004 |
| WO | WO2005004753 A1 | 1/2005 |
| WO | WO2004091455 A2 | 2/2005 |
| WO | WO2005046528 A1 | 5/2005 |
| WO | WO2005062980 A1 | 7/2005 |
| WO | WO2005082578 A1 | 9/2005 |
| WO | WO2006005015 A2 | 1/2006 |
| WO | WO2006026371 A1 | 3/2006 |
| WO | WO2006044679 A1 | 4/2006 |
| WO | WO2006086135 A2 | 8/2006 |
| WO | WO2006088712 A1 | 8/2006 |
| WO | WO2006093795 A1 | 9/2006 |
| WO | WO2006117016 A1 | 11/2006 |
| WO | WO2006124649 A2 | 11/2006 |
| WO | WO2006127089 A1 | 11/2006 |
| WO | WO2006127765 A1 | 11/2006 |
| WO | WO2006135831 A1 | 12/2006 |
| WO | WO2006136930 A1 | 12/2006 |
| WO | WO2007009117 A1 | 1/2007 |
| WO | WO2007053243 A2 | 5/2007 |
| WO | WO2007030825 A2 | 6/2007 |
| WO | WO2007071436 A2 | 6/2007 |
| WO | WO2007130537 A1 | 11/2007 |
| WO | WO2006007401 A2 | 1/2008 |
| WO | WO2001021097 A2 | 3/2008 |
| WO | WO2008028569 A1 | 3/2008 |
| WO | WO2008035337 A2 | 3/2008 |
| WO | WO2008047354 A2 | 4/2008 |
| WO | WO2008070797 A2 | 6/2008 |
| WO | WO2008089365 A2 | 7/2008 |
| WO | WO2008138584 A1 | 11/2008 |
| WO | WO2008150529 A1 | 12/2008 |
| WO | WO2009002548 A1 | 12/2008 |
| WO | WO2009024716 A2 | 2/2009 |
| WO | WO2009029199 A1 | 3/2009 |
| WO | WO2009042196 A2 | 4/2009 |
| WO | WO2009045331 A1 | 4/2009 |
| WO | WO2009045338 A1 | 4/2009 |
| WO | WO2009061389 A2 | 5/2009 |
| WO | WO2009091509 A1 | 7/2009 |
| WO | WO2009094188 A2 | 7/2009 |
| WO | WO2009111241 A2 | 9/2009 |

OTHER PUBLICATIONS

EP Communication issued in EP 07112385 dated Jul. 30, 2009.
Extended European Search Report issued in EP 07106697, dated Aug. 21, 2007, 6 pages.
Extended European Search Report issued in EP 07112385, dated Apr. 1, 2008, 11 pages.
Extended European Search Report issued in EP 10168449, dated Aug. 19, 2010, 3 pages.
International Search Report and Written Opinion issued in PCT/US2010/028873, dated Jun. 15, 2010, 11 pages.
Partial European Search Report issued in EP 07112385, dated Jan. 4, 2008, 5 pages.
Minutes of the Oral Proceedings dated Oct. 19, 2011, filed in EP Patent 1690515, 4 pages.
Notice of Appeal dated Dec. 28, 2011 filed in EP Patent 1690515, 3 pages.
Notice of Opposition with Facts, Evidence and Arguments filed in EP Patent 1690515 dated Apr. 30, 2009, 21 pages.
Palacios, "Percutaneous Valve Replacement and Repair, Fiction or Reality?" Journal of American College of Cardiology, vol. 44, No. 8 (2004) pp. 1662-1663.
Pavcnik et al., "Aortic and venous valve for percutaneous insertion," Min. Invas. Ther. & Allied Techol. 2000, vol. 9, pas. 287-292.
Pelton et al., "Medical Uses of Nitinol," Materials Science Forum vols. 327-328, pp. 63-70 (2000).
Response dated Dec. 9, 2009 to the Notice of Opposition filed in EP Patent 1690515 by ATS Medical Inc., 25 pages.
Response dated Mar. 23, 2011 to Summons dated Sep. 16, 2010, filed in EP Patent 1690515, 21 pages.
Response dated Sep. 17, 2012 to Grounds for Appeal dated Feb. 29, 2012, filed in EP Patent 1690515, 48 pages.
Response dated Sep. 17, 2012, Attachment A.
Response dated Sep. 17, 2012, Attachment B.
Roth, Mark, "Old metal heart valve did its job for 42 years", Pittsburgh Post-Gazette, Wednesday Mar. 5, 2008, 3 pages.
Ruiz, "Transcathether Aortic Valve Implantation and Mitral Valve Repair: State of the Art," Pediatric Cardiology, vol. 26, No. 3 (2005).
Saliba, et al, "Treatment of Obstructions of Prosthetic Conduits by Percutaneous Implantation of Stents," Archives des Maldies du Coeur et des Vaisseaux (France), 1999, pp. 591-596.
Stassano et al., "Mid-term results of the valve-on-valve technique for bioprosthetic failure," Eur. J. Cardiothorac. Surg. 2000; 18:453-457.
Statement of Grounds for Appeal dated Feb. 29, 2012, filed in EP Patent 1690515, 41 pages.
Summons dated Apr. 15, 2013 with Facts and Submissions to Date to Attend Oral Proceedings on Nov. 5, 2013, filed in EP Patent 1690515, 13 pages.
Summons dated Sep. 16, 2010 with Facts and Submissions to Date, filed in EP Patent 1690515, 20 pages.

(56) References Cited

OTHER PUBLICATIONS

Webb, et al., "Percutaneous Aortic Valve Implantation Retrograde from the Femoral Artery," Circulation (2006), 1 13;842-850.
Andersen, H.R. et al, "Transluminal implantation of artificial heart valves. Description of a new expandable aortic valve and initial results with implantation by catheter technique in closed chest pigs." Euro. Heart J. (1992) 13:704-708.
Babaliaros, et al., "State of the Art Percutaneous Intervention for the Treatment of Valvular Heart Disease: A Review of the Current Technologies and Ongoing Research in the Field of Percutaneous Heart Valve Replacement and Repair," Cardiology 2007; 107:87-96.
Bailey, "Percutaneous Expandable Prosthetic Valves," In: Topol EJ, ed. Textbook of Interventional Cardiology. vol. II. Second edition. WB Saunders, Philadelphia, 1994:1268-1276.
Block, et al., "Percutaneous Approaches to Valvular Heart Disease," Current Cardiology Reports, vol. 7 (2005) pp. 108-113.
Bonhoeffer, et al, "Percutaneous Insertion of the Pulmonary Valve," Journal of the American College of Cardiology (United States), May 15, 2002, pp. I 664-I 669.
Bonhoeffer, et al, "Percutaneous Replacement of Pulmonary Valve in a Right-Ventricle to Pulmonary-Artery Prosthetic Conduit with Valve Dysfunction," Lancet (England), Oct. 21, 2000, pp. 1403-1405.
Bonhoeffer, et al, "Transcatheter Implantation of a Bovine Valve in Pulmonary Position: A Lamb Study," Circulation (United States), Aug. 15, 2000, pp. 813-816.
Boudjemline, et al, "Images in Cardiovascular Medicine. Percutaneous Aortic Valve Replacement in Animals," Circulation (United States), Mar. 16, 2004.
Boudjemline, et al, "Is Percutaneous Implantation of a Bovine Venous Valve in the Inferior Vena Cava a Reliable Technique to Treat Chronic Venous Insufficiency Syndrome?" Medical Science Monitor—International Medical Journal of Experimental and Clinical Research (Poland), Mar. 2004, pp. BR61-BR66.
Boudjemline, et al, "Off-pump Replacement of the Pulmonary Valve in Large Right Ventricular Outflow Tracts: A Hybrid Approach," Journal of Thoracic and Cardiovascular Surgery (United States), Apr. 2005, pp. 831-837.
Boudjemline, et al, "Percutaneous Aortic Valve Replacement: Will We Get There?" Heart (British Cardiac Society) (England), Dec. 2001, pp. 705-706.
Boudjemline, et al, "Percutaneous Implantation of a Biological Valve in Aortic Position: Preliminary Results in a Sheep Study," European Heart Journal 22, Sep. 2001, p. 630.
Boudjemline, et al, "Percutaneous Implantation of a Biological Valve in the Aorta to Treat Aortic Valve Insufficiency—A Sheep Study," Medical Science Monitor—International Medical Journal of Experimental and Clinical Research (Poland), Apr. 2002, pp. BR113-BR116.
Boudjemline, et al, "Percutaneous Implantation of a Valve in the Descending Aorta in Lambs," European Heart Journal (England), Jul. 2002, pp. 1045-1049.
Boudjemline, et al, "Percutaneous Pulmonary Valve Replacement in a Large Right Ventricular Outflow Tract: An Experimental Study," Journal of the American College of Cardiology (United States), Mar. 17, 2004, pp. 1082-1087.
Boudjemline, et al, "Percutaneous Valve Insertion: A New Approach," Journal of Thoracic and Cardiovascular Surgery (United States), Mar. 2003, pp. 741-742.
Boudjemline, et al, "Stent Implantation Combined with a Valve Replacement to Treat Degenerated Right Ventricle to Pulmonary Artery Prosthetic Conduits," European Heart Journal 22, Sep. 2001, p. 355.
Boudjemline, et al, "Steps Toward Percutaneous Aortic Valve Replacement," Circulation (United States), Feb. 12, 2002, pp. 775-778.
Boudjemline, et al, "The Percutaneous Implantable Heart Valve," Progress in Pediatric Cardiology (Ireland), 2001, pp. 89-93.
Boudjemline, et al, "Transcatheter Reconstruction of the Right Heart," Cardiology in the Young (England), Jun. 2003, pp. 308-311.
Coats, et al, "The Potential Impact of Percutaneous Pulmonary Valve Stent Implantation on Right Ventricular Outflow Tract Re-Intervention," European Journal of Cardio-Thoracic Surgery (England), Apr. 2005, pp. 536-543.
Cribier, A. et al, "Percutaneous Transcatheter Implantation of an Aortic Valve Prosthesis for Calcific Aortic Stenosis: First Human Case Description," Circulation (2002) 3006-3008.
Davidson et al., "Percutaneous therapies for valvular heart disease," Cardiovascular Pathology 15 (2006) 123-129.
Decision Rejecting Opposition dated Oct. 19, 2011, filed in EP Patent 1690515, 22 pages.
Definition of Hinge downloaded from Voculabulary.com, received at the EPO on Dec. 18, 2012, 1 page.
Definition of Hinge, downloaded from www.meriam-webster.com on Jan. 31, 2013, 3 pages.
Definition of Minimum, downloaded from www.meriam-webster.com on Jan. 31, 2013, 2 pages.
European Search Report issued in EP 10183557, dated Apr. 11, 2011, 7 pages.
European Search Report issued in EP App No. 08165227, dated Mar. 13, 2009.
European Search Report issued in EP Application No. 05004289, dated Jun. 2, 2005, 3 pages.
European Search Report issued in EP Application No. 06101425, dated May 3, 2006, 6 pages.
European Search Report issued in EP Application No. 08150075, dated Mar. 27, 2008, 6 pages.
European Search Report issued in EP Application No. 11425029, dated Aug. 17, 2011, 5 pages.
European Search Report issued in EP Application No. 11425030, dated Aug. 10, 2011, 5 pages.
European Search Report issued in EP Publication No. 1570809 (EP App No. 05004289.4), dated Jan. 5, 2007, 5 pages.
Extended European Search Report issued in EP 09179414, dated Oct. 18, 2010, 8 pages.
Extended European Search Report issued in EP Application 09158822, dated Sep. 29, 2009, 5 pages.
Hanzel, et al., "Complications of percutaneous aortic valve replacement: experience with the CriberEdwards™ percutaneous heart valve," EuroIntervention Supplements (2006), I (Supplement A) A3-A8.
Huber, et al., "Do Valved Stents Compromise Coronary Flow?" Eur. J. Cardiothorac. Surg. 2004;25:754-759.
International Search Report and Written Opinion issued in PCT/IB2012/050604, dated Jul. 26, 2012, 16 pages.
International Search Report and Written Opinion issued in PCT/IB2012/050608, dated Jul. 24, 2012, 9 pages.
International Search Report issued in International Application No. PCT/I B2006/000967, published as WO2006/085225, dated Jul. 6, 2006.
Khambadkone, "Nonsurgical Pulmonary Valve Replacement: Why, When, and How?" Catheterization and Cardiovascular Interventions—Official Journal of the Society for Cardiac Angiography & Interventions (United States), Jul. 2004, pp. 401-408.
Khambadkone, et al, "Percutaneous Implantation of Pulmonary Valves," Expert Review of Cardiovascular Therapy (England), Nov. 2003, pp. 541-548.
Khambadkone, et al, "Percutaneous Pulmonary Valve Implantation: Early and Medium Term Results," Circulation 108 (17 Supplement), Oct. 28, 2003, p. 1V-375.
Khambadkone, et al, "Percutaneous Pulmonary Valve Implantation: Impact of Morphology on Case Selection," Circulation 108 (17 Supplement), Oct. 28, 2003, p. IV-642-IV-643.
Lutter, et al, "Percutaneous Aortic Valve Replacement: An Experimental Study. I. Studies on Implantation," The Journal of Thoracic and Cardiovascular Surgery, Apr. 2002, pp. 768-776.
Lutter, et al, "Percutaneous Valve Replacement: Current State and Future Prospects," Annals of Thoracic Surgery (Netherlands), Dec. 2004, pp. 2199-2206.
Ma, Ling, et al., "Double-crowned valved stents for off-pump mitral valve replacement," European Journal of Cardio Thoracic Surgery, 28:194-198, 2005.

(56) References Cited

OTHER PUBLICATIONS

Medtech Insight, "New Frontiers in Heart Valve Disease," vol. 7, No. 8 (2005).
European Search Report issued in EP Application No. 11425310, completed May 31, 2012, 8 pages.
Grube, Eberhard, et al. Percutaneous Implantation of the Core Valve Self-Expanding Valve Prosthesis in High-Risk Patients With Aortic Valve Disease: The Siegburg First-in-Man Study. American Heart Association, Circulation, 114:1616-1624, 2006.

* cited by examiner

Fig_1

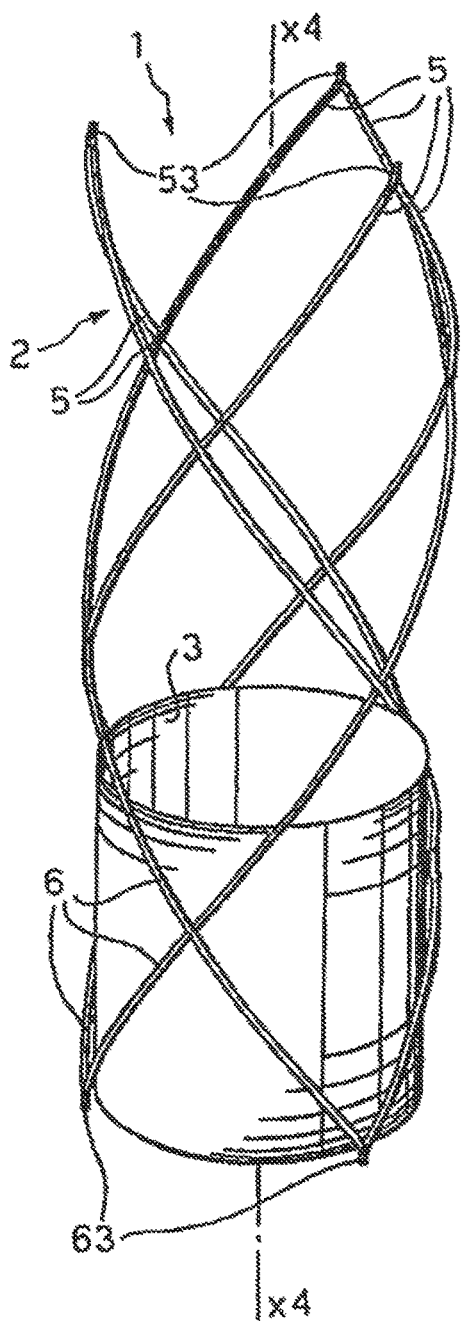
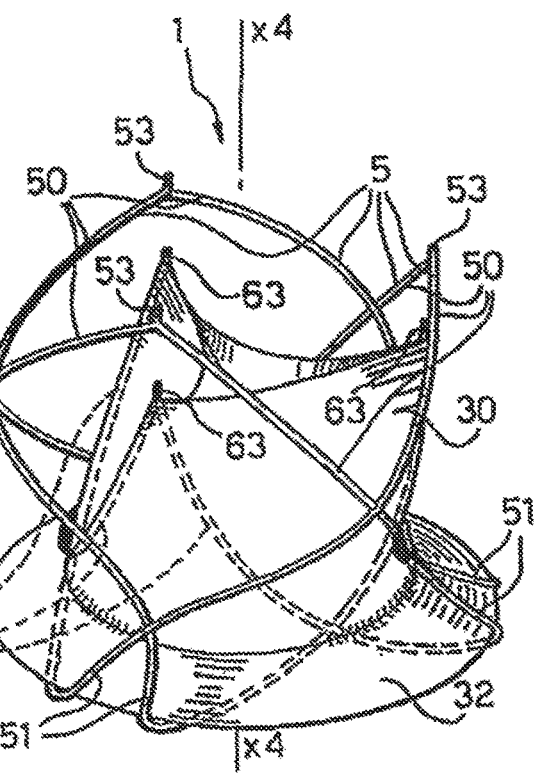

US 9,867,695 B2

MINIMALLY-INVASIVE CARDIAC-VALVE PROSTHESIS

CROSS REFERENCE TO RELATED APPLICATION

This application is a continuation of U.S. application Ser. No. 12/139,683, filed Jun. 16, 2008, now, U.S. Pat. No. 8,535,373, entitled "Minimally-Invasive Cardiac-Valve Prosthesis," which is a continuation of U.S. application Ser. No. 11/066,346, filed Feb. 25, 2005, now, U.S. Pat. No. 8,109,996, entitled "Minimally-Invasive Cardiac-Valve Prosthesis," which claims priority under 35 U.S.C §119 from Italian patent application number TO2004/A000135, filed on Mar. 3, 2004, all of which are hereby incorporated by reference.

TECHNICAL FIELD

The present invention relates to cardiac-valve prostheses. More specifically, the present invention is directed to a prosthesis that is amenable to minimally-invasive implantation.

BACKGROUND

Recently, there has been increasing consideration given to the possibility of using, as an alternative to traditional cardiac-valve prostheses, valves designed to be implanted using minimally-invasive surgical techniques or endovascular delivery (the so-called "percutaneous valves"). Implantation of a percutaneous valve (or implantation using thoracic-microsurgery techniques) is a far less invasive act than the surgical operation required for implanting traditional cardiac-valve prostheses. Further details of exemplary percutaneous implantation techniques are provided in U.S. Publication 2002/0042651, U.S. Pat. No. 3,671,979, and U.S. Pat. No. 5,954,766, which are hereby incorporated by reference.

These prosthetic valves typically include an anchoring structure, which is able to support and fix the valve prosthesis in the implantation position, and prosthetic valve elements, generally in the form of leaflets or flaps, which are stably connected to the anchoring structure and are able to regulate blood flow.

Furthermore, the methods of implantation of valves via a percutaneous route or by means of thoracic microsurgery are very frequently irrespective of the effective removal of the natural valve leaflets. Instead, the cardiac valve may be introduced in a position corresponding to the natural annulus and deployed in situ by simply divaricating definitively the natural valve leaflets.

There is a need for a percutaneous valve that does not run the risk of being displaced (dislodged) with respect to the implantation position, as a result of the hydraulic thrust exerted by the blood flow. There is a further need for a percutaneous valve that secures tightly to the flow duct generally defined by the natural valve annulus, such that it resists blood flow around the outside of the percutaneous valve structure.

SUMMARY

In an exemplary embodiment, the invention described herein is based on the concept of separating, in the framework of the supporting armature of the valve, the function of anchorage of the valve in the implantation site (including the possible function of sealing the valve with respect to the blood-flow duct natural to the region in which the valve is implanted) and the valve function proper. In a preferred way, this purpose is achieved by providing, within the armature of the valve, two structures (which are functionally distinct, but which in effect may be structurally integrated with one another), which are delegated separately to the accomplishment of these two functions. These two structures or portions comprise an external portion which can be spread out to enable anchorage of the cardiac-valve prosthesis at the implantation site, and an internal portion, which is substantially axially coextensive with the external portion, for supporting the prosthetic valve leaflets. The valve thus obtained is adapted in a particularly advantageous way to be implanted in a position corresponding to the so-called Valsalva's sinuses.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

BRIEF DESCRIPTION OF THE DRAWINGS

FIGS. 3 and 4 illustrate a second exemplary embodiment of a prosthetic valve according to the invention.

Figure 1:
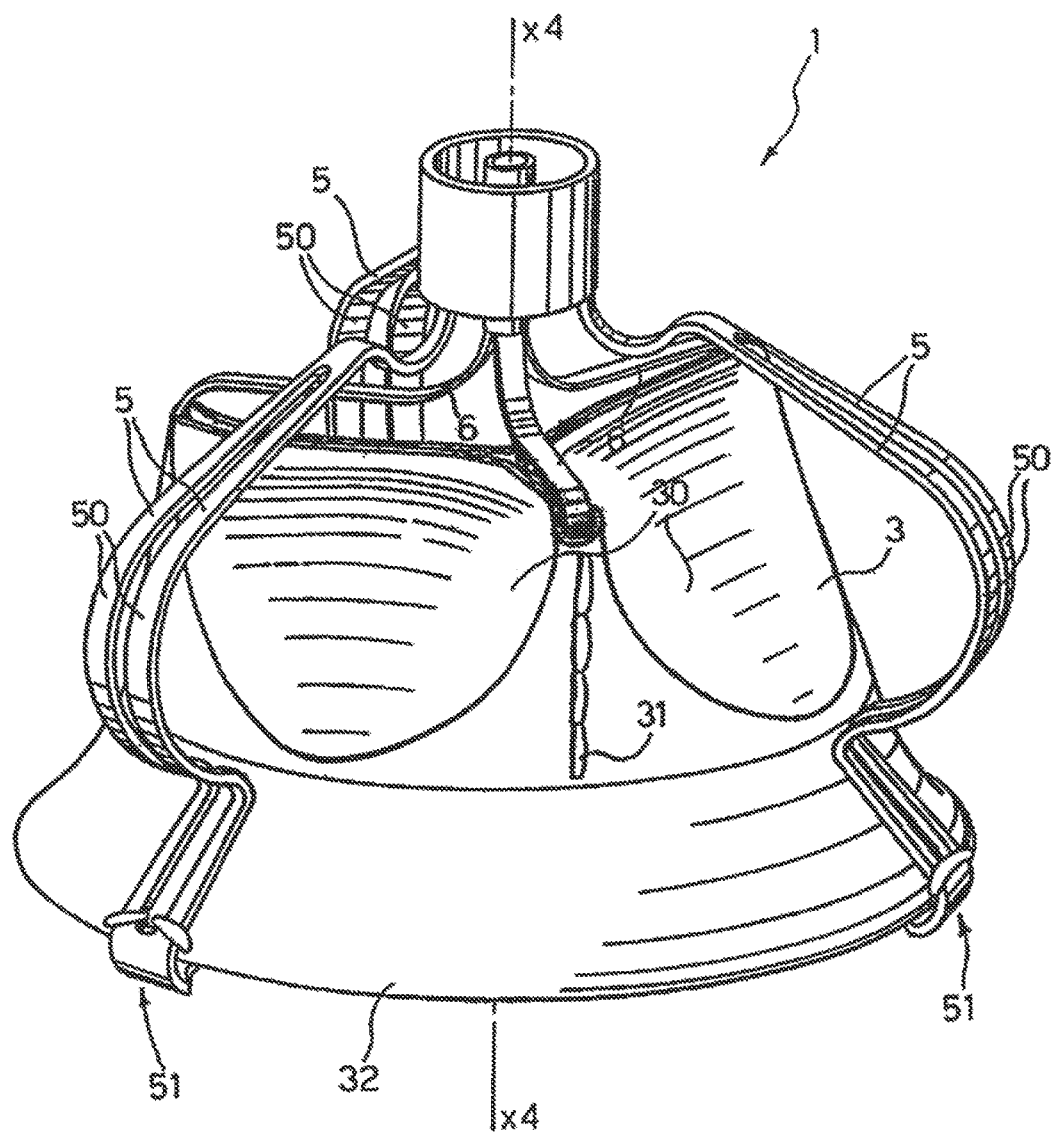
FIG. 1 is a general perspective view of a prosthetic valve according to the invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

In the figures, the reference number 1 designates as a whole a cardiac valve, which can be implanted via percutaneous route or resorting to thoracic-microsurgery techniques. These percutaneous implantation techniques are generally known in the art, and include those techniques described in the documents referenced above.

Figure 2:
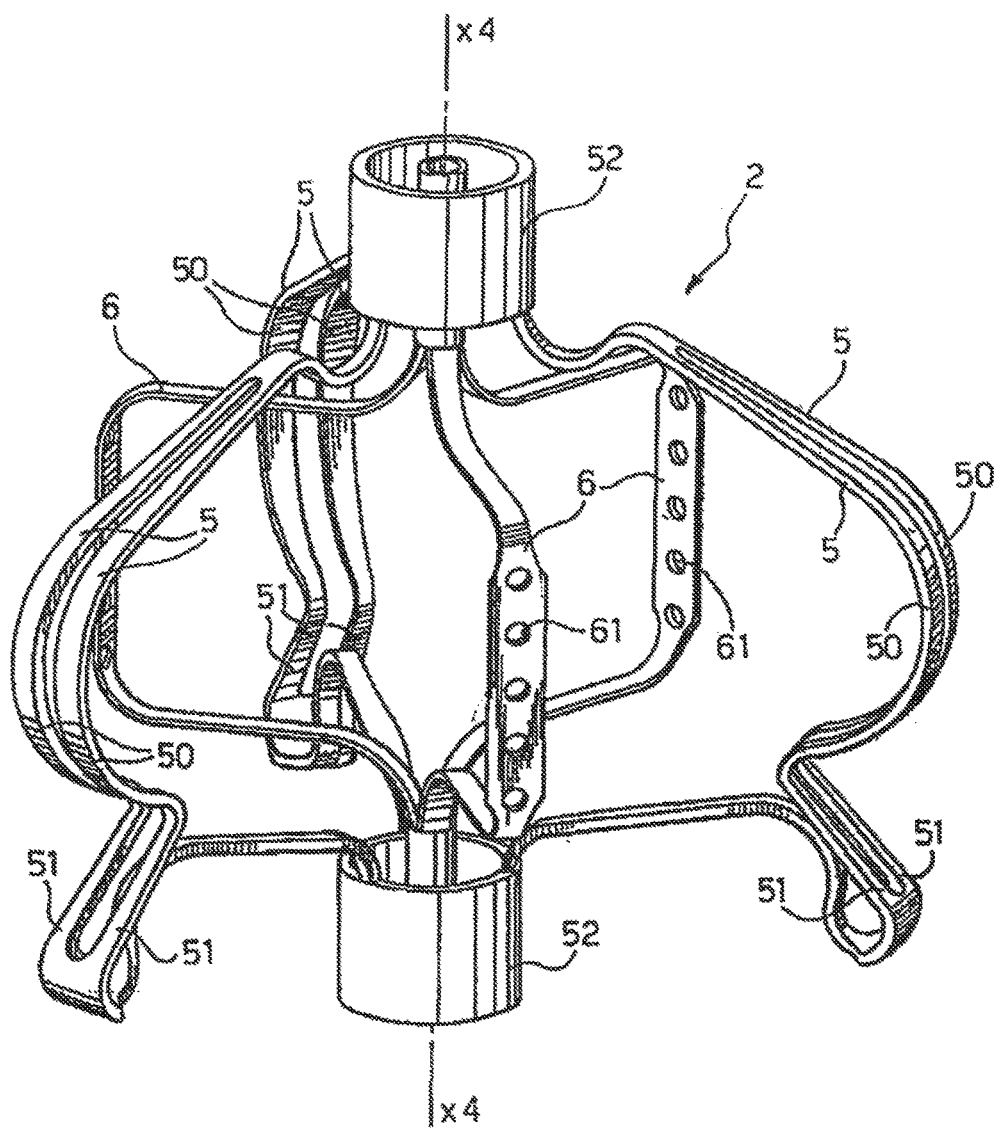
FIG. 2 illustrates the corresponding armature of the valve without the leaflets.

The valve 1 represented in FIGS. 1 and 2 is basically made up of two elements, namely an armature 2, having the characteristics that emerge more clearly from the representation of FIG. 2, and a set of leaflets 3, coupled to the armature 2. The characteristics of the leaflets 3 may be appreciated more fully from the view of FIG. 1.

As shown in FIG. 2, the armature 2 of the valve has a general cage-like structure comprising a set of ribs that extend with a general symmetry of a cylindrical type about a principal axis X4. In percutaneous valves, the axis X4 usually corresponds to the principal axis of the distal part of the catheter used for implantation of the valve 1. For the present purposes, the axis X4 can be viewed basically as an entity of a purely geometrical nature, even though it can in effect be identified either with elements of the implantation catheter or with elements of the armature 2 of the valve 1.

The armature 2 includes a distinguishable first and a second series of ribs designated, respectively, by the reference numbers 5 and 6. These ribs are usually made of metal material that is able to present characteristics of radial expandability, both as a result of a positive action of a dilatation or divarication force exerted by, for example, a balloon catheter and as a result of characteristics proper to the material constituting the ribs 5 (and possibly 6). In particular, the ribs may be made of a superelastic material and/or a material with shape-memory characteristics. A material that is well known in biomedical applications and that presents these characteristics is the material known as Nitinol.

Structures that may substantially be likened to cages, which can be introduced into a vessel of the human body and in particular into a venous site and can then be dilated in loco via dilatation of a distal part of the introducing catheter or, in the case of materials with shape-memory characteristics or the like, as a result of the retraction of a sheath that maintains the structure in a compressed position, are well known in the art. For example, these structures are well known in stent technology and, in particular, the technology of stents for angioplasty.

Due to the possibility of providing cage-like structures with ribs extending with a profile more or less shaped in diametral planes with reference to a principal axis, such as for example the axis X4, further reference may be made to technologies adopted for the fabrication of devices for the mapping or passivation of endocardial sites, such as, typically, endocavitary sites, used for localization and/or treatment of the so-called ectopic sites characteristic of the pathological conditions of a fibrillative type.

The distinction made between the ribs 5 and 6 is based on the fact that, within the armature 2, these different sets of ribs are designed to perform different functions, regardless of whether the ribs constitute physically distinct parts or are different portions of a unitary structure within the armature 2. In particular, the ribs 5 form an external part or anchor portion of the armature 2 designed (see FIG. 1) to enable the location and anchorage of the valve 1 at the implantation site. The ribs 6 are designed to constitute a more internal part or support portion of the armature 2, specifically the part that is to support the valve leaflets 30 of the prosthesis. Essentially, the ribs 5 and 6 are designed to define, within the armature 2, an external portion (ribs 5), which can be spread out or radially expanded to enable anchorage of the prosthesis 1 in the implantation site and an internal portion (ribs 6), which supports the prosthetic valve leaflets 30 provided in the set of leaflets 3.

An important characteristic of the solution described herein is provided by the fact that the two portions of the armature 2 are "substantially axially coextensive" with respect to one another. This definition is understood to indicate synthetically the fact that the two portions occupy, in the direction of the axis X4, axial stretches that are substantially coincident with one another. This is in direct contrast with solutions such as the one described, for example, in the U.S. Pat. No. 6,482,228, which illustrates a valve comprising two homologous portions that are totally staggered with respect to one another in an axial direction so that they can be located, one in a proximal position and the other in a distal position with respect to the coronary ostia.

The ribs 5, which in what follows are designated also as "external" ribs, are preferably arranged in sets of ribs, said sets being typically arranged in threes or multiples of three so as to be more readily adaptable, in a complementary way, to the anatomy of the Valsalva's sinuses, which is the site of choice for implantation of the valve 1.

In an exemplary embodiment, within the ribs 5 there is distinguishable a top part or top branch 50 and a bottom part or bottom branch 51. In the implantation position, the top parts or branches 50 are able, when they are in the deployed or expanded position, to extend within the so-called Valsalva's sinuses. The Valsalva's sinuses are the dilatations, from the overall lobed profile, which are present at the root of the aorta, hence in a physiologically distal position with respect to the aortic valve annulus. The bottom portions or branches 51 (see FIG. 1) are instead designed to extend in a proximal position with respect to the valve annulus so as to extend for a certain stretch within the ventricular chamber.

As a whole, the top parts 50 of the ribs 5, when brought into the extended position, jointly define a tripodal structure, which, by expanding within the Valsalva's sinuses, enables attainment of a condition of firm anchorage of the valve 1. This avoids the possibility of the valve 1, once implanted, being dislodged or even just displaced with respect to the implantation position, as a result of the hydraulic stresses applied thereto during operation by the blood flow.

The anchorage of the valve 1 in the implantation site is further reinforced by the fact that the area of radiusing between the top branches 50 and the bottom branches 51 of the ribs 5 has, precisely on account of the general divaricated or flared pattern of the bottom branches 51, an area of convexity that is thus positioned astride of the valve annulus, reinforcing the condition of shape fit between the armature of the valve and the implantation site. In the schematic representation of the figures, the natural valve leaflets of the valve that is to be replaced with the prosthetic valve 1 are not specifically illustrated.

The valve 1 described herein can be located in situ regardless of whether the natural valve leaflets have previously been removed or (and in a way that is from certain points of view preferred), without proceeding to the removal of said natural valve leaflets, by simply introducing the valve within the valve orifice and thus bringing about, as a result of the divarication of the valve 1 structure, the corresponding definitive divarication of the natural valve leaflets that are brought into, and maintained in, a position of substantial adherence to the surrounding portion of the valve annulus.

The particular conformation of the ribs 5, and in particular of the parts 50 and 51 just described, corresponds to the solution envisaged for the implantation of the valve 1 in the aortic site. Similar structures can be adopted for implantations, for example, in the mitral site.

The top and bottom branches 50 and 51 may in actual fact present conformations that are altogether different from the ones illustrated. For example, the top branches 50 may possibly present a conformation that is approximately symmetrical to the conformation represented herein with reference to the bottom branches 51, thus conferring on the external part of the armature of the valve 2 an overall hourglass conformation. Moreover, the presence of both of the branches 50 and 51 is altogether optional.

Again, in the exemplary embodiment illustrated herein, the terminal top ends of the branches 50 and the bottom ends of the branches 51 are connected to collar parts 52, which are designed to be fitted around, and usually to slide along the principal axis X4 during divarication of the armature 2. This solution proves advantageous as regards to the simplicity and the structural congruence of the armature 2. Recourse thereto should, however, be reconciled with the need to prevent the collar parts 52 from possibly ending up playing an excessive role of obstruction in regard to the blood flow that is to pass (from below upwards, with reference to the configuration of implantation as represented in FIG. 1) through the central orifice of the valve 1 defined between the valve leaflets 30 in a divaricated position. For example, it is conceivable to use just one of the collars 52, for example the one illustrated in the bottom portion in FIG. 2.

The structure and the configuration of the ribs 6 is, as a whole, akin to that of the ribs 5. In the case of the ribs 6, which form the internal part of the armature 2 of the valve 1, there is, however, usually the presence of just three elements that support, in a position corresponding to homologous lines of commissure (which take material form as sutures 31 passing through openings 61 provided on the elements 6), the valve leaflets 30. Essentially, the complex of ribs 6 and valve leaflets 30 is designed to form the normal structure of a biological valve prosthesis. This is a valve prosthesis which (in the form that is to be implanted with a surgical operation of a traditional type, hence of an invasive nature) has met with a wide popularity in the art.

The structural details of biological valve prostheses, consisting of a tubular structure made of biological material (for example, the pericardium or meningeal tissue of animal origin) subjected to treatments of passivation (with gluteraldehyde or similar compounds) or alternatively a biocompatible synthetic material, after prior possible shaping of the cusp-like areas that are to constitute the prosthetic valve leaflets 30, are well known in the art. For further details of the structure of such a valve, reference can be made to EP-B-0 155 245, which is hereby incorporated by reference. For further details of the technology of fabrication and/or treatment of the material of the prosthetic valve leaflets, useful reference can be made to EP-B-0 133 420, which is hereby incorporated by reference.

In addition to the more strictly "valve" part comprising the prosthetic valve leaflets 30 supported in a commissural position by the ribs 6 of the armature 2, the leaflet part of the prosthesis illustrated also has an apron-like part 32, which extends according to a general chimney-like or flared configuration and is supported by the bottom parts 51 of the external ribs 5 of the armature 2. For this purpose, the bottom parts 51 have an overall V-shaped structure, hence comprising two branches that are to enclose within them the chimney-like portion 32 of the set of leaflets 3 of the valve armature 2, so causing this to be divaricated at the moment of spreading out of the valve and maintained in said divaricated position in the intraventricular site in a proximal position with respect to the valve annulus.

Albeit conserving an extreme structural simplicity, from which there derives a corresponding reliability during implantation, the valve structure described manages to meet in an excellent way various needs that in themselves contrast with one another. This is obtained basically by separating the two parts of the armature 2, which are functionally distinct, even though they may be integrated in a single structure, and hence delegating to them two different functions.

In particular, the external ribs 5 (and more specifically when these are present in the two branches 50 and 51, which can be positioned astride of the valve annulus) provide the firm anchorage of the valve in situ, so preventing it from possibly being removed or even just displaced from the implantation site chosen by the person carrying out the implantation operation. This is obtained with a structure that is able to adapt to the natural anatomical conformation without exerting thereon stresses of a traumatic nature.

As shown in the Figures, the ribs 5 can present a rather thin or light structure. This allows them to adhere to the walls of the root of the aorta, to the surrounding portion of the valve annulus, and to the walls of the endocardial chamber, without exerting particularly marked stresses on those walls, which—in extreme cases—could even be at the basis of phenomena of lesions and, even more, of onset of reactions of the organism in regard to said lesions. The action of anchorage is in fact achieved, more than for any other reason, on account of the presence of numerous ribs 5 and their conformation, which is complementary with respect to that of the implantation site (in particular, when this is represented by the Valsalva's sinuses).

The internal part of the armature 2, represented by the ribs 6, enables, spreading out and support of the prosthetic valve leaflets 30 in the implantation position. This is achieved by recourse to a structure and a conformation which, precisely because they reproduce very closely those of traditional prosthetic valves of a biological type, prove particularly suitable and efficient for performing substitution of a defective natural valve. In particular, it is well known that valve prostheses of a biological type, precisely because they are able to reproduce closely the fluid-dynamic characteristics and the characteristics of behaviour of the leaflets of natural cardiac valves, can be used to benefit patients affected by forms of rather marked cardiac insufficiency. This possibility is achieved in an optimal way in the solution described herein precisely because the valve function is rendered altogether independent of the function of anchorage in situ of the prosthesis.

The presence of the branches 51 in the armature 2 of the prosthesis and, conversely, of the apron-like or chimney-like portion 32 in the set of leaflets 3 (in addition to contributing further to the shape fit and hence to the anchorage in the implantation site of the valve 1) likewise enables very efficient channelling of the blood flow coming from the heart, channelling it in a practically complete way, precisely on account of the divaricated or flared configuration of the chimney-like portion 32 within the flow duct defined within the valve leaflets 30. There is thus minimized (and in effect cancelled out) shortly following implantation, the possibility of there being created lines of blood flow that pass on the outside of the cardiac-valve prosthesis.

The foregoing likewise envisages that the two parts or portions of armature 2 are substantially axially coextensive with respect to one another, occupying, if viewed in their development in the direction of the axis X4, axial stretches substantially coinciding with one another. This characteristic enables a precise positioning of the prosthetic valve leaflets in a "physiological" location (i.e., in a location basically corresponding to the location of the natural valve leaflets), likewise benefiting, for the purposes of the anchorage of the prosthesis in situ, from a shape fit with the Valsalva's sinuses.

FIGS. 3 and 4 illustrate a second exemplary embodiment of a cardiac valve, according to the present invention. From a general structural standpoint, the valve of FIGS. 3 and 4 derives basically from the structure of the valve shown in FIGS. 1 and 2. The valve according to FIGS. 3 and 4 is obtained by recourse, as regards the armature, to a single element of tubular shape and reticular structure. In particular, FIG. 3 illustrates this tubular element in an "extroverted" or "extended" configuration, whereas in FIG. 4 the same element is illustrated in an "introverted" configuration, corresponding to the final conformation of implantation of the valve.

In this particular embodiment, the two parts or portions of the armature 2 (the external portion 5 for anchorage of the valve 1 in the implantation site and the internal portion 6 with the function of supporting the valve leaflets) are integrated in a single structure consisting precisely of the tubular element referred to previously. This element, designated as a whole by reference numeral 2, has a substantially cylindrical structure that develops about a principal axis X4 and consists of ribs having a general helical conformation and presenting joints in pairs 53 and 63 at the two ends. The armature 2 is without any discontinuity between the external portion 5 and the internal portion 6 of the ribs. The ribs that form the armature 2 in this embodiment are basically made of a superelastic material and/or shape-memory material.

The valve 1 passes from the extroverted configuration (FIG. 3) to the introverted or final configuration (FIG. 4) through a mechanism of deformation that may be obtained at the implantation site. This can occur, in the case of percutaneous valves, via remote manipulation devices associated to the catheter for introduction of the valve. Said devices are in themselves known in so far as they are used in association with catheters of various types, for example to obtain actions of selective spreading out of implantation devices, such as stents, stent-grafts or the like.

The mechanism of deployment (i.e., introversion) in question involves passing from the extended conformation of FIG. 3 to the final conformation of FIG. 4, thereby causing the joints 63, to which the set of leaflets 3 are fixed (internally with respect to the original cylindrical tubular element), to converge within the tubular structure and then advance therein until the joints 63 arrive in the proximity of the joints 53, which, at the start of the movement of introversion described, were exactly at the opposite end of the original cylindrical tubular element.

Basically, this movement causes the tubular element 2 to pass between an extroverted configuration (FIG. 3), in which said tubular element has a substantially cylindrical shape, with the external portion 5 and internal portion 6 of the armature axially juxtaposed with respect to one another, and a final introverted configuration (FIG. 4), in which the external portion 5 and internal portion 6 are substantially axially coextensive with respect to one another.

This overall movement is usually accompanied by at least a slight divarication of the joints 53 and of the areas of the armature of the valve (external part 5) adjacent thereto. This divarication of the joints 53 and of the areas of the armature adjacent thereto is clearly perceptible in FIG. 4. In the same figure there is moreover perceptible the action of "pinching" of the apron-like part of the leaflet, which may be achieved with a positive action of deformation of the armature and/or by exploiting the shape-memory characteristics of the constituent material. Also in this case, a final configuration is reached, in which the external portion 5 and internal portion 6 of the armature 2 of the valve 1 are substantially axially coextensive with respect to one another, finding themselves occupying axial stretches that substantially coincide with respect to the axis X4.

In the introverted configuration (see FIG. 4), it is possible to distinguish top branches 50 and bottom branches 51 of the ribs 5, in a conformation suitable for being implanted in the Valsalva's sinuses. The top branches 50 extend in a generally cage-like form, which is complementary with the lobed anatomy of the Valsalva's sinuses and co-operate with the bottom branches 51, which are to extend in a proximal position with respect to the valve annulus so as to be introduced within the ventricular chamber, ensuring a firm anchorage of the valve 1 at the implantation site. The set of leaflets 3 comprises the prosthetic valve leaflets 30 supported by the internal ribs 6 and an apron-like part 32 supported by and fixed to the bottom branches 51 of the external ribs 5.

Various modifications and additions can be made to the exemplary embodiments discussed without departing from the scope of the present invention. Accordingly, the scope of the present invention is intended to embrace all such alternatives, modifications, and variations as fall within the scope of the claims, together with all equivalents thereof.

We claim:

1. A method of repairing a native aortic valve, the method comprising:
   positioning a cardiac valve prosthesis at an implantation site corresponding to the location of the native aortic valve, the cardiac valve prosthesis including an armature and a set of valve leaflets, the armature having a first end portion distal to the set of valve leaflets, an opposite second end portion proximal to the set of valve leaflets, a principal axis extending longitudinally through the first end portion and the second end portion, a plurality of valve support ribs extending longitudinally from the first end portion to the second end portion, and a plurality of anchoring ribs, wherein each of the plurality of anchoring ribs extends longitudinally from the first end portion to the second end portion, the set of valve leaflets coupled to and supported by the valve support ribs; and
   allowing the armature to expand such that each of the plurality of anchoring ribs arches longitudinally radially outward from the principal axis to anchor the cardiac valve prosthesis at the implantation site.

2. The method of claim 1, wherein positioning the cardiac valve prosthesis at the implantation site includes positioning the cardiac valve prosthesis at the implantation site with the armature in a radially compressed condition.

3. The method of claim 2, wherein the steps of positioning the cardiac valve prosthesis at the implantation site and allowing the armature to expand are performed without first removing leaflets of the native aortic valve.

4. The method of claim 1, wherein the plurality of anchoring ribs include three sets of anchoring ribs spaced about the principal axis of the cardiac valve prosthesis, each set of anchoring ribs located so as to extend into and adhere to a respective one of a Valsalva sinus located distal to the native aortic valve when the armature is allowed to expand.

5. The method of claim 4, wherein the plurality of valve support ribs includes three valve support ribs spaced about the principal axis of the cardiac valve prosthesis, the valve support ribs defining lines of commissure of the set of valve leaflets.

6. The method of claim 5, wherein each of the valve support ribs includes a generally straight portion.

7. The method of claim 1, wherein each of the plurality of anchoring ribs includes a top part and a bottom part, and wherein allowing the armature to expand includes allowing the armature to expand such that the top part of each of the anchoring ribs arches longitudinally radially outward and extends into a respective Valsalva sinus.

8. The method of claim 7, wherein allowing the armature to expand includes allowing the armature to expand such that the bottom part of each of the anchoring ribs extends partially into a ventricular chamber proximal to an annulus of the native aortic valve.

9. The method of claim 8, wherein positioning the cardiac valve prosthesis includes positioning the cardiac valve prosthesis such that the top and bottom parts of the anchoring ribs are positioned astride the annulus of the native aortic valve.

10. The method of claim 1, wherein the armature is made of a material having shape-memory characteristics, and wherein allowing the armature to expand includes retracting a sheath maintaining the armature in a compressed condition.

11. The method of claim 10, wherein the material having shape-memory characteristics is nitinol.

12. The method of claim 1, wherein allowing the armature to expand includes radially expanding the armature using a balloon catheter.

13. The method of claim 1, wherein positioning the cardiac valve prosthesis includes introducing the cardiac valve prosthesis using a catheter.

14. The method of claim 1, wherein allowing the armature to expand includes allowing the armature to expand such that each of the plurality of anchoring ribs arches longitudinally radially outward and extends into and conforms to a wall of a respective Valsalva sinus.

15. The method of claim 1, wherein the cardiac valve prosthesis further includes a flared portion configured to channel blood flow through a flow duct defined by the set of valve leaflets.

16. A method of repairing a native aortic valve, the method comprising:
    positioning a cardiac valve prosthesis at an implantation site corresponding to the location of the native aortic valve, the cardiac valve prosthesis including an armature and a set of valve leaflets, the armature having a first end portion, an opposite second end portion, a principal axis extending through the first end portion and the second end portion, a plurality of valve support ribs extending between the first end portion and the second end portion, and a plurality of anchoring ribs, wherein each of the plurality of anchoring ribs is directly connected to the first end portion and to the second end portion and extends from the first end portion to the second end portion, the set of valve leaflets coupled to and supported by the valve support ribs; and
    allowing the armature to radially expand such that each of the plurality of anchoring ribs includes a top portion, a bottom portion, and an intermediate portion that arches radially outward from and coplanar with the top portion and the bottom portion and with the principal axis to anchor the cardiac valve prosthesis at the implantation site.

17. The method of claim 16, wherein positioning the cardiac valve prosthesis at the implantation site includes positioning the cardiac valve prosthesis at the implantation site with the armature in a radially compressed condition.

18. The method of claim 17, wherein the steps of positioning the cardiac valve prosthesis at the implantation site and allowing the armature to radially expand are performed without first removing leaflets of the native aortic valve.

19. The method of claim 17, wherein allowing the armature to radially expand includes retracting a sheath maintaining the armature in the radially compressed condition.

20. The method of claim 19, wherein allowing the armature to radially expand includes allowing the armature to radially expand such that each of the plurality of anchoring ribs arches radially outward and extends into a respective Valsalva sinus.

* * * * *